(12) United States Patent
Hogg et al.

(10) Patent No.: US 9,682,234 B2
(45) Date of Patent: Jun. 20, 2017

(54) IMPLANTABLE ELECTRO-MEDICAL DEVICE PROGRAMMABLE FOR IMPROVED OPERATIONAL LIFE

(71) Applicant: EndoStim, Inc., St. Louis, MO (US)

(72) Inventors: Bevil Hogg, Murrieta, CA (US);
Virender K. Sharma, Paradise Valley, AZ (US); Shai Policker, Tenafly, NJ (US); Paul V. Goode, Round Rock, TX (US); Kaila Raby, Albuquerque, NM (US)

(73) Assignee: EndoStim, Inc., St. Louis, MO (US)

( * ) Notice: Subject to any disclaimer, the term of this patent is extended or adjusted under 35 U.S.C. 154(b) by 0 days.

(21) Appl. No.: 14/943,772

(22) Filed: Nov. 17, 2015

(65) Prior Publication Data
US 2016/0136419 A1    May 19, 2016

Related U.S. Application Data

(60) Provisional application No. 62/080,793, filed on Nov. 17, 2014.

(51) Int. Cl.
*A61N 1/00* (2006.01)
*A61N 1/36* (2006.01)
(Continued)

(52) U.S. Cl.
CPC ......... *A61N 1/36007* (2013.01); *A61N 1/378* (2013.01); *G01R 31/3606* (2013.01);
(Continued)

(58) Field of Classification Search
CPC .............. A61N 1/3787; A61N 1/36125; A61N 1/3975; A61N 1/3981
See application file for complete search history.

(56) References Cited

U.S. PATENT DOCUMENTS 3,909,883 A    10/1975    Fegen
3,910,281 A    10/1975    Kletschka
(Continued)

FOREIGN PATENT DOCUMENTS

CN    1476339        2/2004
CN    1494451 A      5/2004
(Continued)

OTHER PUBLICATIONS

Second Office Action for Chinese Patent Application No. 201280028867.7, dated Mar. 21, 2016.
(Continued)

*Primary Examiner* — Robert N Wieland
(74) *Attorney, Agent, or Firm* — Novel IP

(57) ABSTRACT

A device for electrically stimulating one or more anatomical target sites in a patient and for use in the treatment of a plurality of biological conditions of the patient. The device has a pulse generator providing electrical stimulation to the anatomical target sites; a power source for powering the pulse generator; stimulator electrodes connected to the pulse generator for stimulating the anatomical target sites; one or more optional sensing electrodes for monitoring physiological parameters with reference to the anatomical target sites; and a microprocessor programmed to vary a plurality of therapy protocol parameters governing the electrical stimulation to thereby modify operational life parameters of the power source.

23 Claims, 12 Drawing Sheets

(51) Int. Cl.
  *G01R 31/36* (2006.01)
  *G06F 1/32* (2006.01)
  *A61N 1/378* (2006.01)
  *A61N 1/37* (2006.01)

(52) U.S. Cl.
  CPC ........ *G06F 1/3203* (2013.01); *A61N 1/36125* (2013.01); *A61N 1/36135* (2013.01); *A61N 1/3708* (2013.01); *A61N 1/3787* (2013.01)

(56) References Cited

U.S. PATENT DOCUMENTS

| | | |
|---|---|---|
| 4,393,883 A | 7/1983 | Smyth |
| 4,414,986 A | 11/1983 | Dickhudt |
| 4,612,934 A | 9/1986 | Borkan |
| 4,735,205 A | 4/1988 | Chachques |
| 5,117,827 A | 6/1992 | Stuebe |
| 5,188,104 A | 2/1993 | Wernicke |
| 5,193,539 A | 3/1993 | Schulman |
| 5,197,491 A | 3/1993 | Anderson |
| 5,231,988 A | 8/1993 | Wernicke |
| 5,263,480 A | 11/1993 | Wernicke |
| 5,292,344 A | 3/1994 | Douglas |
| 5,360,428 A | 11/1994 | Hutchinson, Jr. |
| 5,423,872 A | 6/1995 | Cigaina |
| 5,531,778 A | 7/1996 | Maschino |
| 5,540,730 A | 7/1996 | Terry, Jr. |
| 5,556,425 A | 9/1996 | Hewson |
| 5,606,242 A | 2/1997 | Hull |
| 5,633,573 A | 5/1997 | van Phuoc |
| 5,649,902 A | 7/1997 | Yoon |
| 5,674,205 A | 10/1997 | Pasricha |
| 5,690,691 A | 11/1997 | Chen |
| 5,697,375 A | 12/1997 | Hickey |
| 5,709,224 A | 1/1998 | Behl |
| 5,716,385 A | 2/1998 | Mittal |
| 5,716,392 A | 2/1998 | Bourgeois |
| 5,810,810 A | 9/1998 | Tay |
| 5,836,994 A | 11/1998 | Bourgeois |
| 5,861,014 A | 1/1999 | Familoni |
| 5,861,044 A | 1/1999 | Crenshaw |
| 5,882,340 A | 3/1999 | Yoon |
| 5,893,883 A | 4/1999 | Torgerson |
| 5,935,126 A | 8/1999 | Riza |
| 5,995,872 A | 11/1999 | Bourgeois |
| 6,006,755 A | 12/1999 | Edwards |
| 6,026,326 A | 2/2000 | Bardy |
| 6,041,258 A | 3/2000 | Cigaina |
| 6,051,017 A | 4/2000 | Loeb |
| 6,091,992 A | 7/2000 | Bourgeois |
| 6,097,984 A | 8/2000 | Douglas |
| 6,216,039 B1 | 4/2001 | Bourgeois |
| 6,221,039 B1 | 4/2001 | Durgin |
| 6,243,607 B1 | 6/2001 | Mintchev |
| 6,254,598 B1 | 7/2001 | Edwards |
| 6,285,897 B1 | 9/2001 | Kilcoyne |
| 6,321,124 B1 | 11/2001 | Cigaina |
| 6,360,130 B1 | 3/2002 | Duysens |
| 6,381,495 B1 | 4/2002 | Jenkins |
| 6,449,511 B1 | 9/2002 | Mintchev |
| 6,510,332 B1 | 1/2003 | Greenstein |
| 6,542,776 B1 | 4/2003 | Gordon |
| 6,571,127 B1 | 5/2003 | Ben-Haim |
| 6,587,719 B1 | 7/2003 | Barrett |
| 6,591,137 B1 | 7/2003 | Fischell |
| 6,611,715 B1 | 8/2003 | Boveja |
| 6,612,983 B1 | 9/2003 | Marchal |
| 6,615,084 B1 | 9/2003 | Cigaina |
| 6,678,561 B2 | 1/2004 | Forsell |
| 6,684,104 B2 | 1/2004 | Gordon |
| 6,749,607 B2 | 6/2004 | Edwards |
| 6,754,536 B2 | 6/2004 | Swoyer |
| 6,760,626 B1 | 7/2004 | Boveja |
| 6,820,019 B1 | 11/2004 | Kelly |
| 6,826,428 B1 | 11/2004 | Chen |
| 6,832,114 B1 | 12/2004 | Whitehurst |
| 6,853,862 B1 | 2/2005 | Marchal |
| 6,876,885 B2 | 4/2005 | Swoyer |
| 6,879,859 B1 | 4/2005 | Boveja |
| 6,879,861 B2 | 4/2005 | Benz |
| 6,901,295 B2 | 5/2005 | Sharma |
| 6,915,165 B2 | 7/2005 | Forsell |
| 6,947,792 B2 | 9/2005 | Ben-Haim |
| 6,952,613 B2 | 10/2005 | Swoyer |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,203,551 B2 | 4/2007 | Houben |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,363,084 B2 | 4/2008 | Kurokawa |
| 7,444,183 B2 | 10/2008 | Knudson |
| 7,477,994 B2 | 1/2009 | Sunshine |
| 7,519,431 B2 | 4/2009 | Goetz |
| 7,519,433 B2 | 4/2009 | Foley |
| 7,558,629 B2 | 7/2009 | Keimel |
| 7,593,777 B2 | 9/2009 | Gerber |
| 7,599,736 B2 | 10/2009 | DiLorenzo |
| 7,620,454 B2 | 11/2009 | Dinsmoor |
| 7,664,551 B2 | 2/2010 | Cigaina |
| 7,676,270 B2 | 3/2010 | Imran |
| 7,702,394 B2 | 4/2010 | Imran |
| 7,702,395 B2 | 4/2010 | Towe |
| 7,711,437 B1 | 5/2010 | Bornzin |
| 7,720,539 B2 | 5/2010 | Mintchev |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,809,442 B2 | 10/2010 | Bolea |
| 7,813,809 B2 | 10/2010 | Strother |
| 7,835,796 B2 | 11/2010 | Maschino |
| 7,848,802 B2 | 12/2010 | Goetz |
| 7,899,540 B2 | 3/2011 | Maschino |
| 7,914,468 B2 | 3/2011 | Shalon |
| 7,941,221 B2 | 5/2011 | Foley |
| 7,957,807 B2 | 6/2011 | Starkebaum |
| 7,962,214 B2 | 6/2011 | Byerman |
| 7,983,755 B2 | 7/2011 | Starkebaum |
| 8,135,470 B2 | 3/2012 | Keimel |
| 8,155,758 B2 | 4/2012 | Roline |
| 8,160,709 B2 | 4/2012 | Soffer |
| 8,185,206 B2 | 5/2012 | Starkebaum |
| 8,282,561 B2 | 10/2012 | Towe |
| 8,380,321 B2 | 2/2013 | Goetz |
| 8,406,868 B2 | 3/2013 | Buschman |
| 8,423,134 B2 | 4/2013 | Buschman |
| 8,447,403 B2 | 5/2013 | Sharma |
| 8,447,404 B2 | 5/2013 | Sharma |
| 8,452,407 B2 | 5/2013 | Whitehurst |
| 8,467,874 B2 | 6/2013 | Chen |
| 8,467,884 B2 | 6/2013 | Chen |
| 8,521,292 B2 | 8/2013 | Wei |
| 8,538,532 B2 | 9/2013 | Starkebaum |
| 8,538,534 B2 | 9/2013 | Soffer |
| 8,543,210 B2 | 9/2013 | Sharma |
| 8,556,952 B2 | 10/2013 | Shadduck |
| 8,594,811 B2 | 11/2013 | Chen |
| 8,712,529 B2 | 4/2014 | Sharma |
| 8,712,530 B2 | 4/2014 | Sharma |

(56) References Cited

U.S. PATENT DOCUMENTS

| | | | |
|---|---|---|---|
| 8,718,771 B2 * | 5/2014 | Gandhi | A61N 1/3708 320/132 |
| 8,761,903 B2 | 6/2014 | Chen | |
| 8,792,986 B2 | 7/2014 | Cigaina | |
| 8,831,737 B2 | 9/2014 | Wesselink | |
| 8,892,217 B2 | 11/2014 | Camps | |
| 9,020,597 B2 | 4/2015 | Sharma | |
| 9,061,147 B2 | 6/2015 | Sharma | |
| 2001/0041831 A1 | 11/2001 | Starkweather | |
| 2002/0103522 A1 | 8/2002 | Swoyer | |
| 2002/0138075 A1 | 9/2002 | Edwards | |
| 2002/0161414 A1 | 10/2002 | Flesler | |
| 2002/0165589 A1 | 11/2002 | Imran | |
| 2003/0014086 A1 | 1/2003 | Sharma | |
| 2003/0028226 A1 | 2/2003 | Thompson | |
| 2003/0055463 A1 | 3/2003 | Gordon | |
| 2003/0078633 A1 | 4/2003 | Firlik | |
| 2003/0120321 A1 | 6/2003 | Bumm | |
| 2003/0144708 A1 | 7/2003 | Starkebaum | |
| 2003/0195600 A1 | 10/2003 | Tronnes | |
| 2004/0012088 A1 | 1/2004 | Fukasawa | |
| 2004/0015201 A1 | 1/2004 | Greenstein | |
| 2004/0024428 A1 | 2/2004 | Barrett | |
| 2004/0039427 A1 | 2/2004 | Barrett | |
| 2004/0044376 A1 | 3/2004 | Flesler | |
| 2004/0059393 A1 | 3/2004 | Policker | |
| 2004/0073453 A1 | 4/2004 | Nenov | |
| 2004/0088033 A1 | 5/2004 | Smits | |
| 2004/0116977 A1 | 6/2004 | Finch | |
| 2004/0138586 A1 | 7/2004 | Ganz | |
| 2004/0147976 A1 | 7/2004 | Gordon | |
| 2004/0167583 A1 | 8/2004 | Knudson | |
| 2004/0172088 A1 | 9/2004 | Knudson | |
| 2004/0186544 A1 | 9/2004 | King | |
| 2004/0193229 A1 | 9/2004 | Starkebaum | |
| 2004/0243182 A1 | 12/2004 | Cohen | |
| 2005/0027328 A1 | 2/2005 | Greenstein | |
| 2005/0049655 A1 | 3/2005 | Boveja | |
| 2005/0065571 A1 | 3/2005 | Imran | |
| 2005/0070974 A1 | 3/2005 | Knudson | |
| 2005/0075678 A1 | 4/2005 | Faul | |
| 2005/0090873 A1 | 4/2005 | Imran | |
| 2005/0131486 A1 | 6/2005 | Boveja | |
| 2005/0137480 A1 | 6/2005 | Alt | |
| 2005/0137643 A1 | 6/2005 | Mintchev | |
| 2005/0137644 A1 | 6/2005 | Boveja | |
| 2005/0143787 A1 | 6/2005 | Boveja | |
| 2005/0149141 A1 | 7/2005 | Starkebaum | |
| 2005/0149142 A1 | 7/2005 | Starkebaum | |
| 2005/0149146 A1 | 7/2005 | Boveja | |
| 2005/0222637 A1 | 10/2005 | Chen | |
| 2005/0222638 A1 | 10/2005 | Foley | |
| 2005/0245788 A1 | 11/2005 | Gerber | |
| 2005/0251219 A1 | 11/2005 | Evans | |
| 2006/0004304 A1 | 1/2006 | Parks | |
| 2006/0015162 A1 | 1/2006 | Edward | |
| 2006/0036293 A1 | 2/2006 | Whitehurst | |
| 2006/0064037 A1 | 3/2006 | Shalon | |
| 2006/0074459 A1 | 4/2006 | Flesler | |
| 2006/0095077 A1 | 5/2006 | Tronnes | |
| 2006/0106442 A1 | 5/2006 | Richardson | |
| 2006/0116736 A1 | 6/2006 | DiLorenzo | |
| 2006/0167498 A1 | 7/2006 | DiLorenzo | |
| 2006/0200217 A1 | 9/2006 | Wessman | |
| 2006/0206160 A1 | 9/2006 | Cigaina | |
| 2006/0218011 A1 | 9/2006 | Walker | |
| 2006/0247717 A1 | 11/2006 | Starkebaum | |
| 2006/0247718 A1 | 11/2006 | Starkebaum | |
| 2006/0247722 A1 | 11/2006 | Maschino | |
| 2006/0265021 A1 | 11/2006 | Herbert | |
| 2007/0016274 A1 | 1/2007 | Boveja | |
| 2007/0049793 A1 | 3/2007 | Ignagni | |
| 2007/0060955 A1 | 3/2007 | Strother | |
| 2007/0060968 A1 | 3/2007 | Strother | |
| 2007/0060979 A1 | 3/2007 | Strother | |
| 2007/0066995 A1 | 3/2007 | Strother | |
| 2007/0067000 A1 | 3/2007 | Strother | |
| 2007/0100388 A1 | 5/2007 | Gerber | |
| 2007/0106337 A1 | 5/2007 | Errico | |
| 2007/0106338 A1 | 5/2007 | Errico | |
| 2007/0114971 A1 | 5/2007 | Uesaka | |
| 2007/0142699 A1 | 6/2007 | Jandrall | |
| 2007/0142831 A1 | 6/2007 | Shadduck | |
| 2007/0142884 A1 | 6/2007 | Jandrall | |
| 2007/0156182 A1 | 7/2007 | Castel | |
| 2007/0162084 A1 | 7/2007 | Chen | |
| 2007/0162085 A1 | 7/2007 | DiLorenzo | |
| 2007/0179542 A1 | 8/2007 | Prakash | |
| 2007/0238942 A1 | 10/2007 | Baylor | |
| 2007/0239248 A1 | 10/2007 | Hastings | |
| 2007/0244375 A1 | 10/2007 | Jenkins | |
| 2007/0255118 A1 | 11/2007 | Miesel | |
| 2007/0255335 A1 | 11/2007 | Herbert | |
| 2007/0255336 A1 | 11/2007 | Herbert | |
| 2007/0255352 A1 | 11/2007 | Roline | |
| 2007/0265662 A1 | 11/2007 | Ufford | |
| 2007/0265666 A1 | 11/2007 | Roberts | |
| 2007/0265668 A1 | 11/2007 | Reinke | |
| 2007/0265671 A1 | 11/2007 | Roberts | |
| 2007/0265674 A1 | 11/2007 | Olson | |
| 2007/0282410 A1 | 12/2007 | Cross | |
| 2007/0293910 A1 | 12/2007 | Strother | |
| 2008/0021512 A1 | 1/2008 | Knudson | |
| 2008/0039904 A1 | 2/2008 | Bulkes | |
| 2008/0046062 A1 | 2/2008 | Camps | |
| 2008/0058836 A1 | 3/2008 | Moll | |
| 2008/0058891 A1 | 3/2008 | Ben-Haim | |
| 2008/0086179 A1 | 4/2008 | Sharma | |
| 2008/0132968 A1 | 6/2008 | Starkebaum | |
| 2008/0147137 A1 | 6/2008 | Cohen | |
| 2008/0154191 A1 | 6/2008 | Gobel | |
| 2008/0183238 A1 | 7/2008 | Chen | |
| 2008/0195171 A1 | 8/2008 | Sharma | |
| 2008/0208355 A1 | 8/2008 | Stack | |
| 2009/0012421 A1 | 1/2009 | Bek | |
| 2009/0018617 A1 | 1/2009 | Skelton | |
| 2009/0018619 A1 | 1/2009 | Skelton | |
| 2009/0020406 A1 | 1/2009 | Nirmalakhandan | |
| 2009/0030475 A1 | 1/2009 | Brynelsen | |
| 2009/0069803 A1 | 3/2009 | Starkebaum | |
| 2009/0076498 A1 | 3/2009 | Saadat | |
| 2009/0088817 A1 | 4/2009 | Starkebaum | |
| 2009/0131993 A1 | 5/2009 | Rousso | |
| 2009/0132001 A1 | 5/2009 | Soffer | |
| 2009/0187223 A1 | 7/2009 | Gross | |
| 2009/0204063 A1 | 8/2009 | Policker | |
| 2009/0264951 A1 | 10/2009 | Sharma | |
| 2009/0281553 A1 | 11/2009 | Kalloo | |
| 2010/0004648 A1 | 1/2010 | Edwards | |
| 2010/0049026 A1 | 2/2010 | Gerber | |
| 2010/0057085 A1 | 3/2010 | Holcomb | |
| 2010/0069789 A1 | 3/2010 | Hirota | |
| 2010/0076345 A1 | 3/2010 | Soffer | |
| 2010/0170812 A1 | 7/2010 | Odierno | |
| 2010/0198039 A1 | 8/2010 | Towe | |
| 2010/0268495 A1 | 10/2010 | Armstrong | |
| 2010/0324432 A1 | 12/2010 | Bjoerling | |
| 2011/0004266 A1 | 1/2011 | Sharma | |
| 2011/0046653 A1 | 2/2011 | Addington | |
| 2011/0071589 A1 | 3/2011 | Starkebaum | |
| 2011/0213437 A9 | 9/2011 | Armstrong | |
| 2011/0224665 A1 | 9/2011 | Crosby | |
| 2011/0295335 A1 | 12/2011 | Sharma | |
| 2011/0295336 A1 | 12/2011 | Sharma | |
| 2011/0307027 A1 | 12/2011 | Sharma | |
| 2011/0307028 A1 | 12/2011 | Sharma | |
| 2012/0232610 A1 | 9/2012 | Soffer | |
| 2012/0259389 A1 | 10/2012 | Starkebaum | |
| 2012/0265103 A1 | 10/2012 | Policker | |
| 2012/0277619 A1 | 11/2012 | Starkebaum | |
| 2013/0030503 A1 | 1/2013 | Yaniv | |
| 2013/0035740 A1 | 2/2013 | Sharma | |
| 2013/0072928 A1 | 3/2013 | Schaer | |
| 2013/0090551 A1 | 4/2013 | Sharma | |

(56) References Cited

U.S. PATENT DOCUMENTS

| | | | |
|---|---|---|---|
| 2013/0178912 | A1 | 7/2013 | Sharma |
| 2013/0218229 | A1 | 8/2013 | Sharma |
| 2013/0231660 | A1 | 9/2013 | Edwards |
| 2013/0238048 | A1 | 9/2013 | Almendinger |
| 2014/0012348 | A1 | 1/2014 | Starkebaum |
| 2014/0018657 | A1 | 1/2014 | Sharma |
| 2014/0088664 | A1 | 3/2014 | Sharma |
| 2014/0088666 | A1 | 3/2014 | Goetz |
| 2014/0135886 | A1 | 5/2014 | Cook |
| 2014/0222106 | A1 | 8/2014 | Sharma |
| 2014/0228911 | A1 | 8/2014 | Sharma |
| 2014/0243593 | A1 | 8/2014 | Goode |
| 2015/0045786 | A1 | 2/2015 | Edwards |
| 2015/0119952 | A1 | 4/2015 | Sharma |
| 2016/0001071 | A1 | 1/2016 | Sharma |

FOREIGN PATENT DOCUMENTS

| | | |
|---|---|---|
| CN | 102725021 | 10/2012 |
| EP | 1004330 | 5/2000 |
| WO | 9853878 | 12/1998 |
| WO | 9903532 | 1/1999 |
| WO | 9930776 | 6/1999 |
| WO | 0061223 | 10/2000 |
| WO | 0061223 A1 | 10/2000 |
| WO | 0061224 | 10/2000 |
| WO | 0061224 A1 | 10/2000 |
| WO | 0243467 | 6/2002 |
| WO | 0243467 A2 | 6/2002 |
| WO | 02089655 | 11/2002 |
| WO | 2005051486 A1 | 9/2005 |
| WO | 2007137026 | 11/2007 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |
| WO | 2015034867 | 3/2015 |
| WO | 2015077425 | 5/2015 |
| WO | 2015077435 | 5/2015 |

OTHER PUBLICATIONS

Shellock, Frank G. 'RF Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.

Stein et al., 'Three-dimensional Imaging of the Lower Esophageal Sphincter in Gastroesophageal Reflux Disease,' Annual Meeting of the American Surgical Association, Apr. 11-13, 1991, 374-383.

Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.

Supplementary European Search Report for EP20120779639, Virender K. Sharma, Nov. 13, 2014.

Tam, Wce et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).

Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.

Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.

Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.

Office Action dated Jun. 8, 2016 for U.S. Appl. No. 14/475,736.
Office Action dated Mar. 15, 2016 for U.S. Appl. No. 14/695,267.
Office Action dated Mar. 17, 2016 for U.S. Appl. No. 14/500,856.
Office Action dated May 20, 2016 for U.S. Appl. No. 13/975,162.
Office Action dated May 4, 2016 for U.S. Appl. No. 14/548,793.
Notice of Allowance dated Jul. 19, 2016 for U.S. Appl. No. 14/191,085.
Supplementary European Search Report for EP13831668, completed on Apr. 15, 2016.
Office Action dated Aug. 24, 2016 for U.S. Appl. No. 14/753,402.
Notice of Allowance mailed Sep. 27, 2016 for U.S. Appl. No. 14/500,856.
Office Action dated Oct. 3, 2016 for U.S. Appl. No. 14/548,793.
Second Office Action for Chines Patent Application No. 201380054290.1, Oct. 26, 2016.
Extended European Search Report for EPO Application No. 16174071.7, Oct. 19, 2016.
International Search Report for PCT/US2015/061108, May 26, 2016.
Christensen et al., 'Physiologic Specialization at Esophagogastric Junction in Three Species', American Journal of Physiology, vol. 225, No. 6, Dec. 1973, 1265-1270.
Cigaina, Valerio; Long-term Follow-Up of Gastric Stimulation for Obesity: The Mestre 8-Year Experience; Obesity Surgery; 14; 2004; S14-22.
Clarke et al,. 'An Endoscopic Implantable Device Stimulates the LES On-Demand by Remote Control in a Canine Model', Gastrointestinal Endoscopy, vol. 63, No. 5; 2006, AB103, 759.
Clarke et al., 'An endoscopically implantable device stimulates the lower esophageal sphincter on demand by remote control: a study using a canine model', Endoscopy 2007; 39: 72-76.
Ellis, et al., 'The Prevention of Experimentally Induced Reflux by Electrical Stimulation of the Distal Esophagus', American Journal of Surgery, vol. 115, Apr. 1968, 482-487.
EPO Search Report EP09704463, Jan. 10, 2011, Virender K. Sharma.
European Search Opinion for EP20120779639, Virender K. Sharma, Nov. 25, 2014.
Examination Report for Australian Patent Application No. 2012242533, Oct. 5, 2015.
Examination Report for Australian Patent Application No. 2012250686, Nov. 4, 2015.
Examination Report for New Zealand Patent Application No. 616944, Jun. 17, 2014.
Examination Report for New Zealand Patent Application No. 616944, Nov. 2, 2015.
Extended European Search Report for EPO Application No. 12771852.6, Aug. 28, 2014.
First Office Action for Application No. CN 01819456, dated Nov. 18, 2014.
First Office Action for Chinese Patent Application No. 201380054290.1, Apr. 1, 2016.
Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.
International Search Report for PCT/US12/053576, Dec. 24, 2012.
International Search Report for PCT/US2007/068907, Aug. 7, 2008.
International Search Report for PCT/US2008/053780, Jun. 8, 2009.
International Search Report for PCT/US2008/056479, Aug. 20, 2008.
International Search Report for PCT/US2011/027243, Jul. 8, 2011.
International Search Report for PCT/US2012/033695, Aug. 7, 2012.
International Search Report for PCT/US2012/036408, Aug. 17, 2012.
International Search Report for PCT/US2013/056520, Apr. 4, 2014.
International Search Report for PCT/US2014/053793, Mar. 27, 2015.
International Search Report for PCT/US2014/066565, Mar. 12, 2015.

(56) References Cited

OTHER PUBLICATIONS

International Search Report for PCT/US2014/066578, Mar. 19, 2015.
Jameison, GG et al. "Laparoscopic Nissen Fundoplication". Annals of Surgery, vol. 220. No. 2, p. 139 (1994).
Kahrilas et al., 'Impact of Fundoplication on Bolus Transit Across Esophagogastric Junction', American Physiological Society, 1998, 1386-1393.
Kamath et al., 'Neurocardiac and Cerebral Responses Evoked by Esophageal Vago-Afferent Stimulation in Humans: Effects of Varying Intensities', Cardiovascular Research, 40 (1998) 591-599.
Kantsevoy et al., 'An Endoscopically Implantable On-Demand Stimulator Is Successful in Increasing Lower Esophageal Sphincter Pressure in a Porcine Model', Gastrointestinal Endoscopy, vol. 61, No. 5: 2005, AB79, 222.
Lund et al., 'Electrical Stimulation of Esophageal Smooth Muscle and Effects of Antagonists', American Journal of Physiology, vol. 217, No. 5, Nov. 1969, 1369-1374.
Notice of Allowance dated Apr. 3, 2014 for U.S. Appl. No. 13/447,168.
Notice of Allowance dated Dec. 24, 2014 for U.S. Appl. No. 13/463,803.
Notice of Allowance dated Feb. 20, 2015 for U.S. Appl. No. 14/201,645.
Notice of Allowance dated Jan. 20, 2015 for U.S. Appl. No. 13/602,184.
Notice of Allowance dated Jan. 20, 2016 for U.S. Appl. No. 14/201,766.
Notice of Allowance dated Jul. 21, 2014 for U.S. Appl. No. 13/447,168.
Notice of Allowance dated Mar. 17, 2014 for U.S. Appl. No. 13/447,168.
Office Action dated Apr. 11, 2014 for U.S. Appl. No. 13/602,184.
Office Action dated Feb. 1, 2016 for U.S. Appl. No. 14/475,736.
Office Action dated Feb. 20, 2015 for U.S. Appl. No. 14/175,927.
Office Action dated Jul. 8, 2014 for U.S. Appl. No. 13/463,803.
Office Action dated Jun. 19, 2015 for U.S. Appl. No. 13/975,162.
Office Action dated Jun. 25, 2015 for U.S. Appl. No. 14/201,766.
Office Action dated Mar. 10, 2016 for U.S. Appl. No. 14/191,085.
Office Action dated Oct. 2, 2015 for U.S. Appl. No. 14/500,856.
Office Action dated Oct. 7, 2015 for U.S. Appl. No. 13/975,162.
Office Action for Chinese Patent Application No. 201280028867.7, May 4, 2015.
Sallam et al, 'Feasibility of gastric electrical stimulation by percutaneous endoscopic transgastric electrodes', Gastrointestinal Endoscopy; vol. 68, No. 4; 2008, 754-759.
Sanmiguel et al, 'Effect of electrical stimulation of the LES on LES pressure in a canine model', Am J Physiol Gastrointest Live Physiol; 295: 389-394; 2008.

* cited by examiner

| 200 | | | | | |
|---|---|---|---|---|---|
| Pulse Type | Pulse Width | Pulse Frequency | Pulse Amplitude | On Cycle | Off Cycle |
| Short Pulse | 1-999 μsec | 1-100 Hz | Low (1-999 μAmp) Intermediate (1-50 mAmp) and any values therein | 0-24 hrs | 0-24 hrs |
| Intermediate Pulse | 1-250 msec | 1-100 Hz | Low (1-999 μAmp) Intermediate (1-50 mAmp) and any values therein | 0-24 hrs | 0-24 hrs |
| Intermediate Pulse | 1-250 msec | 1-59 cpm | Low (1-999 μAmp) Intermediate (1-50 mAmp) and any values therein | 0-24 hrs | 0-24 hrs |
| Long Pulse | 251 msec-1 sec | 1-59 cpm | Low (1-999 μAmp) Intermediate (1-50 mAmp) and any values therein | 0-24 hrs | 0-24 hrs |

FIG. 2

IMPLANTABLE ELECTRO-MEDICAL DEVICE PROGRAMMABLE FOR IMPROVED OPERATIONAL LIFE

CROSS-REFERENCE

The present application relies on U.S. Patent Provisional No. 62/080,793, filed on Nov. 17, 2014, for priority and is hereby incorporated by reference in its entirety.

FIELD

This invention relates generally to an electro-medical device for electrical stimulation of one or more anatomical target sites to treat a plurality of biological conditions. More particularly, this invention relates to an electro-medical device that is programmable for improved operational life with reference to a plurality of desired treatment stimulations or protocols.

BACKGROUND

Electrical stimulation has been suggested for use in the treatment of biological conditions of patient's, such as, obesity and GERD. The treatment typically involves placing stimulator electrodes, of an electro-medical device, at or near an anatomical site in the patient by endoscopic, surgical or radiological procedures. The operational life of such electro-medical devices is contingent upon the service life of the battery or energy source powering the device. The service life of the energy source is in turn affected by the electrical stimulation regimen and therefore a plurality of parameters governing the regimen.

Therefore, there is a need for an electro-medical device that can be programmed for desired or improved operational life benefits in relation to the electrical stimulation or therapy regimen parameters.

SUMMARY

The following embodiments and aspects thereof are described and illustrated in conjunction with systems, tools and methods, which are meant to be exemplary and illustrative, not limiting in scope.

The present specification discloses a device for electrical stimulation of one or more anatomical target sites in a patient and for use in the treatment of a plurality of biological conditions of the patient, said device comprising: a pulse generator providing electrical stimulation to said one or more anatomical target sites, wherein said electrical stimulation comprises a stimulation current; a power source for powering said pulse generator; at least one stimulator electrode connected to said pulse generator for stimulating said one or more anatomical target sites; and, a microprocessor programmed to vary a plurality of therapy protocol parameters governing the electrical stimulation to thereby modify operational life parameters of the power source, wherein the therapy protocol parameters and the operational life of the power source are associated according to the following relations:

$$L_{BAT} = \frac{CAP_{BAT} \cdot eff_{USE}}{I_{BAT}}, \text{ where}$$

$$I_{BAT} = \left[\left[\left(eff_{TH} \cdot I_{TH} \cdot \frac{V_{TH} + V_{OH}}{V_{BAT}} \cdot PRF \cdot PW\right) + I_{SOH}\right] \cdot DC_{TH} + I_{SLP} \cdot (1 - DC_{TH}) + I_{TM}\right];$$

wherein $eff_{TH}$ is a function of an output stimulation circuit current divided by an input stimulation circuit current; wherein $I_{SOH}$ is equal to an amount of current required to run the device and not including the stimulation current; wherein $L_{BAT}$ is a function of power source service life; wherein $CAP_{BAT}$ is a function of power source capacity; wherein $eff_{USE}$ is a function of a usable efficiency of power source; wherein $I_{BAT}$ is a function of power source current; wherein $I_{TH}$ is a function of a level of current exiting the device from an output terminal; wherein $V_{TH}$ is a function of a level of voltage at an output terminal of the device; wherein $V_{OH}$ is a function of an overhead output voltage; wherein $V_{BAT}$ is a function of a power source voltage; wherein PRF is a function of a pulse repetition frequency; wherein PW is a function of a pulse width; wherein $DC_{TH}$ is a function of a duty cycle; wherein $I_{SLP}$ is a function of sleep current; and wherein $I_{TM}$ is a function of average telemetry current.

Optionally, the power source is a battery. The battery may be rechargeable or non-rechargeable. The operational life parameters of the battery may comprise battery capacity, usable efficiency of battery due to end of life efficiency, and battery current.

Optionally, the power source is a capacitor.

The therapy protocol parameters, for an electrical stimulation pulse train, may comprise: number of pulses, shape of pulses, interval between pulse train repetitions, duration of a pulse, timing and amplitude of pulses, amperage to be provided to said one or more anatomical target sites, potential to be provided to said one or more anatomical target sites, and duty cycles.

Optionally, the device further comprises at least one sensor for monitoring at least one physiological parameter of said patient. The microprocessor may modify said therapy protocol parameters based upon physiological information sensed by said at least one sensor.

The present specification also discloses a device for electrical stimulation of one or more anatomical target sites in a patient and for use in the treatment of a plurality of biological conditions of the patient, said device comprising: a pulse generator providing electrical stimulation to said one or more anatomical target sites; a power source for powering said pulse generator; at least one stimulator electrode connected to said pulse generator for stimulating said one or more anatomical target sites; a microprocessor programmed to vary a plurality of therapy protocol parameters governing the electrical stimulation to thereby modify operational life parameters of the power source, wherein the therapy protocol parameters and the operational life of the power source are associated according to the following relations:

$$L_{BAT} = \frac{CAP_{BAT} \cdot eff_{USE}}{I_{BAT}}, \text{ where}$$

$$I_{BAT} = \left[\left[\left(eff_{TH} \cdot I_{TH} \cdot \frac{V_{TH} + V_{OH}}{V_{BAT}} \cdot PRF \cdot PW\right) + I_{SOH}\right] \cdot DC_{TH} + I_{SLP} \cdot (1 - DC_{TH}) + I_{TM}\right];$$

and, at least one sensor connected to said microprocessor for sensing at least one physiological parameter of said patient; wherein $eff_{TH}$ is a function of an output stimulation circuit current divided by an input stimulation circuit current; wherein $I_{SOH}$ is equal to an amount of current required to run the device and not including the stimulation current; wherein $L_{BAT}$ is a function of power source service life; wherein $CAP_{BAT}$ is a function of power source capacity; wherein $eff_{USE}$ is a function of a usable efficiency of power source; wherein $I_{BAT}$ is a function of power source current; wherein $I_{TH}$ is a function of a level of current exiting the device from an output terminal; wherein $V_{TH}$ is a function of a level of voltage at an output terminal of the device; wherein $V_{OH}$ is a function of an overhead output voltage; wherein $V_{BAT}$ is a function of a power source voltage; wherein PRF is a function of a pulse repetition frequency; wherein PW is a function of a pulse width; wherein $DC_{TH}$ is a function of a duty cycle; wherein $I_{SLP}$ is a function of sleep current; and wherein $I_{TM}$ is a function of average telemetry current.

Optionally, the power source is a battery. The battery may be rechargeable or non-rechargeable. The operational life parameters of the battery may comprise battery capacity, usable efficiency of battery due to end of life efficiency, and battery current.

Optionally, the power source is a capacitor.

The therapy protocol parameters, for an electrical stimulation pulse train, may comprise: number of pulses, shape of pulses, interval between pulse train repetitions, duration of a pulse, timing and amplitude of pulses, amperage to be provided to said one or more anatomical target sites, potential to be provided to said one or more anatomical target sites, and duty cycles.

The present specification also discloses a system for electrical stimulation of one or more anatomical target sites in a patient and for use in the treatment of a plurality of biological conditions of the patient, said system comprising: a pulse generator providing electrical stimulation to said one or more anatomical target sites; a power source for powering said pulse generator; at least one stimulator electrode connected to said pulse generator for stimulating said one or more anatomical target sites; and, a microprocessor programmed to vary a plurality of therapy protocol parameters governing the electrical stimulation to thereby modify operational life parameters of the power source, wherein the therapy protocol parameters and the operational life of the power source are associated according to the following relations:

$$L_{BAT} = \frac{CAP_{BAT} \cdot (eff)_{USE}}{I_{BAT}}, \text{ where}$$

$$I_{BAT} = \left[\left[\left(eff_{TH} \cdot I_{TH} \cdot \frac{V_{TH} + V_{OH}}{V_{BAT}} \cdot PRF \cdot PW\right) + I_{SOH}\right] \cdot DC_{TH} + I_{SLP} \cdot (1 - DC_{TH}) + I_{TM}\right]$$

wherein $eff_{TH}$ is a function of an output stimulation circuit current divided by an input stimulation circuit current; wherein $I_{SOH}$ is equal to an amount of current required to run the device and not including the stimulation current; wherein $L_{BAT}$ is a function of power source service life; wherein $CAP_{BAT}$ is a function of power source capacity; wherein $eff_{USE}$ is a function of a usable efficiency of power source; wherein $I_{BAT}$ is a function of power source current; wherein $I_{TH}$ is a function of a level of current exiting the device from an output terminal; wherein $V_{TH}$ is a function of a level of voltage at an output terminal of the device; wherein $V_{OH}$ is a function of an overhead output voltage; wherein $V_{BAT}$ is a function of a power source voltage; wherein PRF is a function of a pulse repetition frequency; wherein PW is a function of a pulse width; wherein $DC_{TH}$ is a function of a duty cycle; wherein $I_{SLP}$ is a function of sleep current; and wherein $I_{TM}$ is a function of average telemetry current.

Optionally, the power source is a battery. The battery may be rechargeable or non-rechargeable.

Optionally, the power source is a capacitor.

Optionally, the system further comprises at least one sensor for monitoring at least one physiological parameter of said patient. The microprocessor may modify said therapy protocol parameters based upon physiological information sensed by said at least one sensor.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 2 shows exemplary therapy protocol parameters;

DETAILED DESCRIPTION

Figure 1:
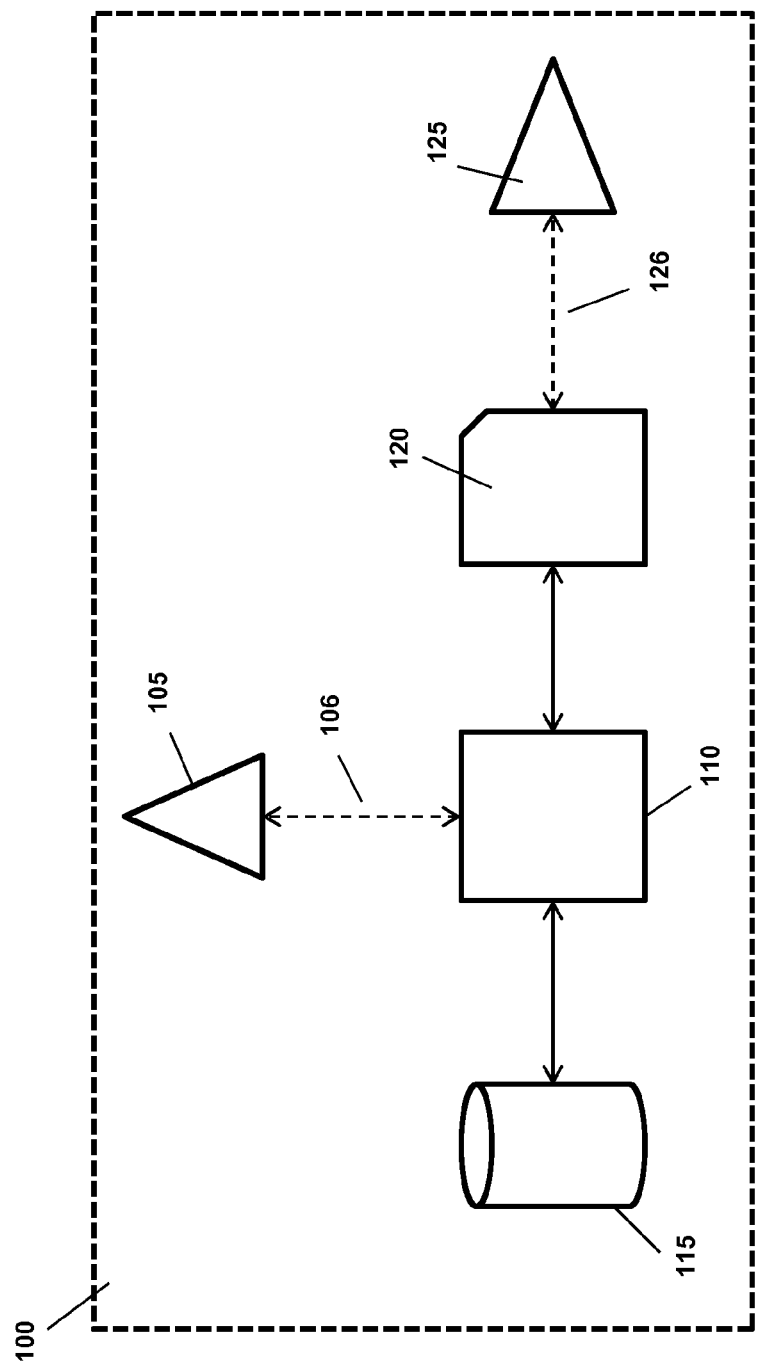
FIG. 1 is a block diagram illustration of an electro-medical device in accordance with an embodiment.

The present invention is directed towards a plurality of operational or therapy protocol parameters with battery parameters for improved or enhanced operational life of a programmable implantable electro-medical device for the treatment of a plurality of biological conditions. The electro-medical device, including macrostimulators or microstimulators, typically employs stimulator electrodes which can be implanted with minimal invasiveness at or near a treatment or stimulation site.

The electro-medical device can be used to treat a plurality of biological conditions and achieve a plurality of different therapeutic objectives: treatment of GERD (gastroesophageal reflux disease); treatment of diurnal GERD; treatment of nocturnal GERD; reducing the frequency of transient lower esophageal relaxation (tLESR) events; reducing acid exposure during tLESR events; normalizing a patient's LES (lower esophageal sphincter) function; treatment of hypotensive LES; increasing resting or baseline LES pressure; treating a patient to normalize esophageal pH; treating a patient to normalize esophageal pH when in the supine position; treating a patient to prevent damage to the patient's lower esophageal sphincter caused by acid reflux; treatment of supine position induced GERD; treatment of activity-induced GERD; prevention of supine position induced GERD; prevention of activity-induced GERD; treating a patient to mitigate damage to the patient's lower esophageal sphincter caused by acid reflux; treating a patient to stop progression of damage to the patient's lower esophageal sphincter caused by acid reflux; treating a patient to minimize transient relaxations of the patient's lower esophageal sphincter; modifying or increasing LES pressure; modifying or increasing esophageal body pressure; modifying or improving esophageal body function; modifying or improving esophageal sensation induced by the refluxate; modifying or improving the volume of refluxate; modifying or improving the clearance of the refluxate; reducing incidents of heartburn; modifying or improving esophageal acid exposure; increasing lower esophageal tone; detecting when a patient swallows; detecting when a patient is eating; treating a gastrointestinal condition of a patient; treating a patient to minimize the patient's consumption of certain solids or liquids; reducing patient symptoms associated with GERD wherein such reduction is measured by an improvement in a patient quality of life survey and wherein an improvement is calculated by having a patient provide a first set of responses to the quality of life survey prior to treatment and having a patient provide a second set of responses to the quality of life survey after the treatment and comparing the first set of responses to the second set of responses; treating a patient for any of the above-listed therapeutic objectives with the additional requirement of avoiding tissue habituation, tissue fatigue, tissue injury or damage, or certain adverse reactions, including, but not limited to, chest pain, difficulty in swallowing, pain associated with swallowing, heartburn, injury to surrounding tissue, or arrhythmias.

The electro-medical device may be implanted within a plurality of anatomical target sites or regions to achieve one or more of the therapeutic objectives described above. Treatment/target sites, or implantation sites, include: the lower esophageal sphincter; proximate the LES or in the vicinity of the LES, wherein proximate or in the vicinity of the LES is defined as +/−3 cm from the LES; the esophageal body; the upper esophageal sphincter (UES); within, proximate to, or in the vicinity of the gastro-esophageal junction; the esophagus, including esophageal body, LES, and UES; proximate the esophagus or in the vicinity of the esophagus, wherein proximate or in the vicinity of the esophagus is defined as +/−3 cm from the esophagus; at or within the stomach; in direct contact with or +/−3 cm from the gastric wall, including the anterior antrum, posterior antrum, anterior corpus, posterior corpus, lesser curvature, greater curvature, anterior fundus, and posterior fundus; in direct contact with or +/−3 cm from the nerves supplying the LES or gastro-esophageal junction; in direct contact with or +/−3 cm from the nerves supplying the esophageal body; in direct contact with or +/−3 cm from the nerves supplying the UES; or in direct contact with or +/−3 cm from the nerves supplying the esophagus, including the esophageal body, LES, and UES.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In one embodiment, the electro-medical device may be a conventional pulse generator, a miniature pulse generator, or a microstimulator.

In one embodiment, any electro-medical device, including a macrostimulator or microstimulator, can be programmed to achieve improved or enhanced operational life of the device while implementing a plurality of desired operational or therapy protocols. It should be appreciated that the relationship/association of operational or therapy protocol parameters with battery parameters, in accordance with an aspect of the present invention, are implemented in an electro-medical device, such as a macrostimulator or microstimulator, having a plurality of electrodes, or at least one electrode, including, but not limited to, unipolar or bipolar electrodes, an energy source, such as a battery, and a microprocessor which stores a plurality of programmatic instructions wherein the instructions, when executed by the device, execute the stimulation therapies while achieving optimized and/or improved operational life of the device.

It should be appreciated that the relationships/associations of operational or therapy protocol parameters with battery parameters described herein, for desired or improved operational life of the battery or electro-medical device, can be used with a plurality of different electro-medical devices, including those electrical stimulation devices disclosed in U.S. patent application Ser. Nos. 13/975,162, 13/661,483, 13/041,063, 13/041,114, 13/447,168, 12/359,317, and 13/463,803, U.S. Pat. Nos. 6,901,295, 6,591,137, 6,774,153, 6,826,428, 7,738,961, 8,447,403, 8,447,404, 8,538,534, and 8,160,709, and PCT Application Numbers PCT/US11/27243 and PCTUS13/56520, all of which are herein incorporated by reference.

FIG. 1 shows an embodiment of an electro-medical device 100 wherein a plurality of stimulator electrodes 105 is provided for placement at or near a treatment or stimulation site. A pulse generator 110 is provided for stimulation of the stimulator electrodes 105 and corresponding portion of the treatment or stimulation site. The pulse generator 110 is connected to a power source 115 for supplying a source of power. The pulse generator 110 is further connected to the stimulator electrodes 105 by wires 106 for applying electrical stimulus to the electrodes 105. Alternatively, the stimulator electrodes 105 may be coupled to the pulse generator 110 in a wireless fashion using an RF link, an ultrasonic link, a thermal link, a magnetic link, an electromagnetic link or an optical link.

The power source 115 can be either a direct current source or an alternating current source. The number of stimulator electrodes 105 is determined by a number of factors, including the size of the electrodes, their power and the size of the desired placement area.

In one embodiment, the pulse generator 110 is controlled by a microprocessor 120 for applying the electrical stimulus for periods of variable duration and variable power/frequency, so as to produce a plurality of treatment stimulations/therapies. In another embodiment, the device does not include a microprocessor.

Additionally or optionally sensing electrodes 125 may be electrically connected by wires 126 to the microprocessor 120. Alternatively, the sensing electrodes 125 may be in wireless communication with the microprocessor 120. The sensing electrodes 125 may be selected to sense one or more physiological parameters with reference to a plurality of anatomical target sites, regions or areas. For example, during a treatment regimen for obesity and/or GERD, while applying electrical stimulation to the upper esophageal sphincter (UES) the sensing electrodes 125 may be placed in the esophagus to sense physical parameters such as esophageal peristalsis, pH, pressure, temperature and impedance. Upon sensing appropriate changes in esophageal peristalsis, pH, pressure, temperature and/or impedance, the electrical stimulation in the upper esophageal sphincter may be initiated so as to contract the upper esophageal sphincter and impede passage of food from the oropharynx into the esophagus, thereby increasing the time of mastication, reducing the food intake and, preferably, increasing stimulation of the satiety centre. In one embodiment, the device 100 does not include sensing electrodes and comprises simply a stimulating arrangement.

The stimulator electrodes 105 may be placed by endoscopic, surgical or radiological procedures.

The stimulus may be triggered by a transmitter (not shown) external to a patient's body, similar to a remote transmitter for a cardiac pacemaker.

In one embodiment, the device 100 is designed as a 'micro' device with all the major components—the stimulator electrodes 105, the sensor electrodes 125, the microcontroller 120, the pulse generator 110 and the power source 115 integrated into a single unit, for easy deployment at any desired location in a patient's body. The microdevice contains an outer shell made of a biocompatible, hermetically sealed material such as glass, ceramic, metal, or polymers. For this purpose, any material may be selected that keeps moisture out yet allows radiofrequency/electromagnetic or magnetic energy to pass through. The outer shell may also be constructed of an acid corrosion resistant material such as a suitable inert polymer. Examples of such materials include: those from the polyolefin family such as HDPE (high density polyethylene), LLDPE (linear low density polyethylene), and UHMWPE (ultra high molecular weight polyethylene); fluoropolymer materials like PTFETM (poly tetrafluoroethylene), FEPTM (fluorinated ethylene propylene) and others; polymethylpentene, and polysulfones; and, some elastomers such as thermoplastic polyurethanes and C-Flex type block copolymers that are stable in acidic environments. Additionally, the outer shell may be constructed of an acid corrosion resistant metal such as platinum, gold, tantalum, titanium, or suitable alloys thereof.

The microdevice may be coated with an antimicrobial agent such as an antibiotic or antifungal agent to prevent infection at the time of implantation. Additionally, the microdevice may be coated with an immunosuppressent such as a steroid, cyclosporine, tacrolimus, azathioprine, mycophenolate mofetil, muromonab CD-3, or antithymocyte globulin to prevent rejection.

In one embodiment, the device 100 has a local energy source 115, such as a battery, that has one or more of the following characteristics: the energy source 115 is rechargeable and has a recharge frequency of once per day for 15 minutes, once per week for approximately 60 minutes, once per month, or once per year; comprises lithium ion battery technology; comprises solid state battery technology; comprises lithium polymer battery technology; comprises super capacitor technology; is not rechargeable; and, is not rechargeable and/or has an implant life of at least one year. In one embodiment, a power management unit is used to convert output voltage from the power supply 115 to the specified level of operating voltage of the microprocessor 120 (and its peripherals).

In one embodiment, the energy source 115 comprises an external power source coupled to the device 100 via a suitable means, such as RF link. In another embodiment, the energy source 115 comprises a self-contained power source utilizing any suitable means of generation or storage of energy. Examples of such a power source include a primary battery, a replenishable or rechargeable battery such as a lithium ion battery, an electrolytic capacitor, and a super- or ultra-capacitor, etc. In case the self-contained energy source is replenishable or rechargeable, any suitable means of replenishing or recharging the power source may be used, such as an RF link, an optical link, a thermal link, or any other energy-coupling link.

In accordance with an aspect of the present specification, the electro-medical device 100 provides enhanced/improved operational life benefits through optimized operational or therapy protocol parameters. To enable improved or desired operational life benefits of the device 100, the present specification associates the operational or therapy protocol parameters of the device 100 to a plurality of battery or power source parameters, such as battery service life, capacity, or current, in accordance with the following equations:

$$L_{BAT} = \frac{CAP_{BAT} \cdot \mathit{eff}_{USE}}{I_{BAT}} \quad \text{Equation A}$$

Where:
$L_{BAT}$ [Hr]=battery or power source service life in hours (Hr)
$CAP_{BAT}$ [mAHr]=battery or power source capacity in milliamps hours (mAHr)
$eff_{USE}$ [%]=usable efficiency of battery or power source due to end of life efficiency (before battery or power source voltage drops too low), allowable depth-of-discharge, or similar events or combination of events.
$I_{BAT}$ [mA]=battery or power source current (current at the battery or power source terminals) in milliamps (mA), where:

$$I_{BAT} = \left[\left[\left(eff_{TH} \cdot I_{TH} \cdot \frac{V_{TH} + V_{OH}}{V_{BAT}} \cdot PRF \cdot PW\right) + I_{SOH}\right] \cdot DC_{TH} + I_{SLP} \cdot (1 - DC_{TH}) + I_{TM}\right]$$ Equation B Where:
$eff_{TH}$ [%]=a general efficiency term for therapy, i.e. (output stimulation circuit current)/(input stimulation circuit current)×100%;
$I_{TH}$ [mA]=therapy current (current exiting the electro-medical device output terminal);
$V_{TH}$ [V]=therapy voltage (voltage at the electro-medical device output terminal);
$V_{OH}$[V]=overhead output voltage (on a constant current output system there is usually the internal voltage that is at least 0.5-2V higher than the output voltage to keep the internals operating in the correct range);
$V_{BAT}$ [V]=battery or power source voltage (average voltage at the battery terminals);
PRF [Hz]=therapy pulse repetition frequency in hertz (Hz);
PW [s]=therapy pulse width in second(s);
$I_{SOH}$ [mA]=stimulation overhead current (there is often a non-scalable power loss associated with the output driver circuitry, thus not part of $eff_{TH}$), i.e. the amount of current dedicated to run the stimulation circuity and which does not include the actual stimulation current itself;
$DC_{TH}$ [%]=therapy duty cycle (average operation time);
$I_{SLP}$ [mA]=sleep current (power when the device is in an "off" state, but is still capable of doing background tests, watchdog, or other basic monitoring); and
$I_{TM}$ [mA]=average telemetry current (can be high depending on telemetry protocol).

A therapy which requires a lower amount of energy increases service life of the battery 115 and therefore the long-term functionality of the electro-medical device 100. Accordingly, the microprocessor 120 can be programmed using the Equations A and B such that the device 100 produces electrical pulses of varying shape, duration and frequency so as to produce the desired stimulation or therapeutic effect while enabling optimization and/or improvement of the operational life of the device 100 (or the battery 115). In one embodiment, for example, using Equations A and B, the microprocessor 120 can be programmed to continuously provide a pulse train of 3 mA, 200 μsec pulses at a rate of 20 Hz (i.e. no duty cycle) with a minimum operational battery life of 5 years. Thus, as would be appreciated by persons of ordinary skill in the art, the operational battery life and therefore of the device can be varied and approximately set to a desired level by varying the operational or therapy protocol parameters.

The output of the device 100, as controlled by the microcontroller 120, can be programmed to vary a plurality of operational or therapy protocol parameters, such as: the number of pulses in a pulse train; the shape of pulses in a pulse train; the interval between pulse train repetitions; the duration of each pulse; the timing and amplitude of pulses in trains; the desired amount of amperage to be provided to an anatomical target site; and, the desired amount of potential to be provided to an anatomical target site, depending upon the load and the current produced.

In addition, the electrical stimulus can be provided continuously or intermittently. For example, one time or more per hour may be suitable in some circumstances.

In various embodiments, the electrical stimulus in the stimulator electrodes 105 may have any shape necessary to produce the desired result, including a square, rectangular, sinusoidal or saw-tooth shape.

In one embodiment, the device 100 can be allowed to engage in automated "on/off" duty cycles that can range, for example, from 1 millisecond to 24 hours. During the "on" period, stimulation is applied for a long enough period to enable recruitment of adequate nerves and/or muscle fibers to achieve a desired pressure, function or effect. The desired "on" period is patient specific and is preferably calculated based on the time required to change a pressure or function of an anatomical target site, such as the LES, from a baseline pressure or function to a desired therapeutic pressure or function plus additional time to maintain the therapeutic pressure (maintenance time) or function. For example, the maintenance time ranges from 1 second to 12 hours. The "off" period is preferably set in order to prevent development of tolerance or muscle fatigue, to improve device functionality, and to optimize energy consumption from the energy source/battery. The desired "off" period ranges, for example, from 1 second to 24 hours. The desired "off" period is patient specific and calculated based on the time required to change a pressure or function of an anatomical target site, such as the LES, from the desired therapeutic pressure or function to a baseline pressure or function plus optional additional time to maintain the baseline pressure (relaxation time) or function. For example, the relaxation time ranges from 1 second to 12 hours.

As an example, the operational or therapy protocol parameters, which are effectuated through an electrical pulse, may comprise any of the variable ranges detailed in the table 200 of FIG. 2. Accordingly, the operational life of the battery and therefore of the electro-medical device can be advantageously estimated for further optimization with reference to the therapy protocol parameters. For example, in one embodiment, an electro-medical device is implanted in a patient with the goal of providing at least one more year of operational life after having already operated for a pre-defined amount of time with a predefined set of parameters. In this example, using the equations above, Lbat is set to 8,760 hours for the goal of one year and the stimulation parameters, including pulse width, pulse frequency, and pulse amplitude are left unchanged with the intention of only changing the duty cycle (DCth). The equations are then rearranged to solve for DCth. Once DCth is calculated, the electro-medical device can be reprogrammed to adjust the duty cycle to reflect the new value.

Figure 3:
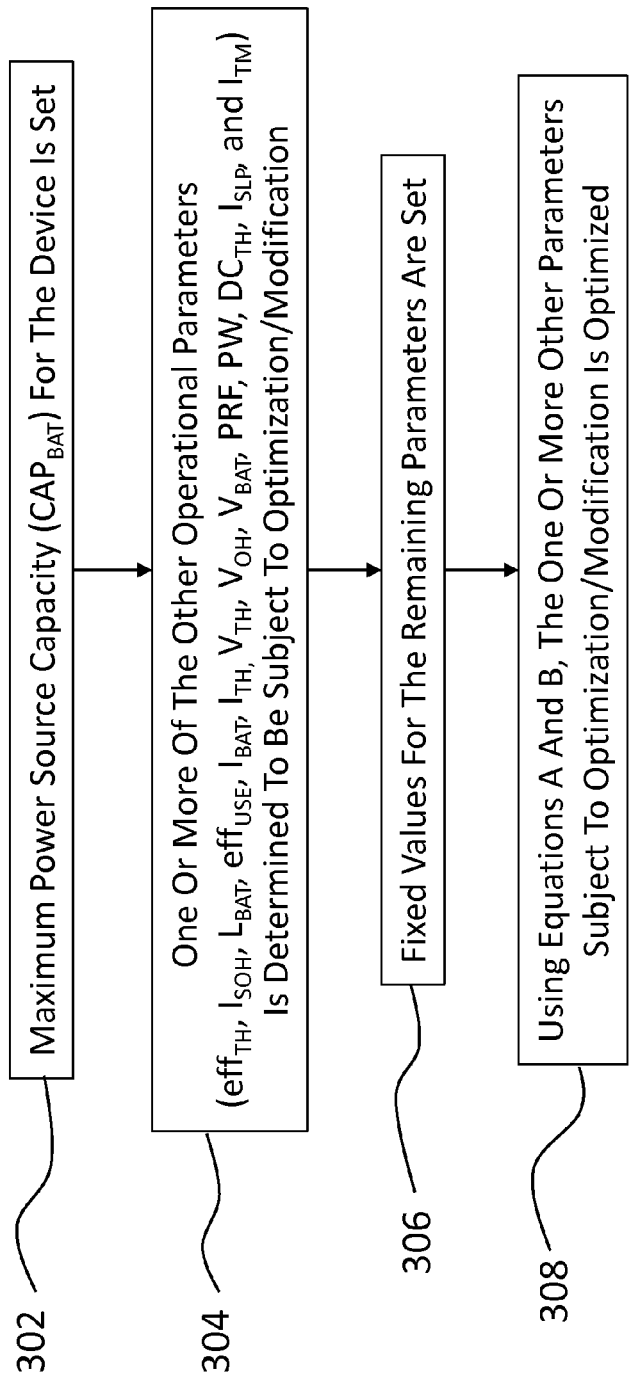
FIG. 3 is a flow chart illustrating the steps involved in one embodiment of setting a maximum power source capacity and optimizing one or more of the other operational parameters of an electro-medical device using the equations of the present specification.

In one embodiment, a maximum power source capacity for the device is set ($CAP_{BAT}$). Additionally, a minority, and preferably only one, of the remaining parameters ($eff_{TH}$, $I_{SOH}$, $L_{BAT}$, $eff_{USE}$, $I_{BAT}$, $I_{TH}$, $V_{TH}$, $V_{OH}$, $V_{BAT}$, PRF, PW, $DC_{TH}$, $I_{SLP}$, and $I_{TM}$) is subject to optimization or modification, with the remainder being a fixed value. Using the maximum power source capacity value and the other fixed values, the minority, or preferably one, of the parameters subject to optimization of modification is then determined using Equations A and B. FIG. 3 is a flow chart illustrating the steps involved in one embodiment of setting a maximum power source capacity and optimizing one or more of the other operational parameters of an electro-medical device using the equations of the present specification. At step 302, the maximum power source capacity ($CAP_{BAT}$) for the device is set. At step 304, one or more of the other parameters ($eff_{TH}$, $I_{SOH}$, $L_{BAT}$, $eff_{USE}$, $I_{BAT}$, $I_{TH}$, $V_{TH}$, $V_{OH}$, $V_{BAT}$, PRF, PW, $DC_{TH}$, $I_{SLP}$, and $I_{TM}$) is determined to be subject to optimization/modification. Then, at step 306, fixed values for the remaining parameters are set. Using equations A and B of the present specification, the one or more other parameters subject to optimization/modification is optimized at step 308.

Figure 4:
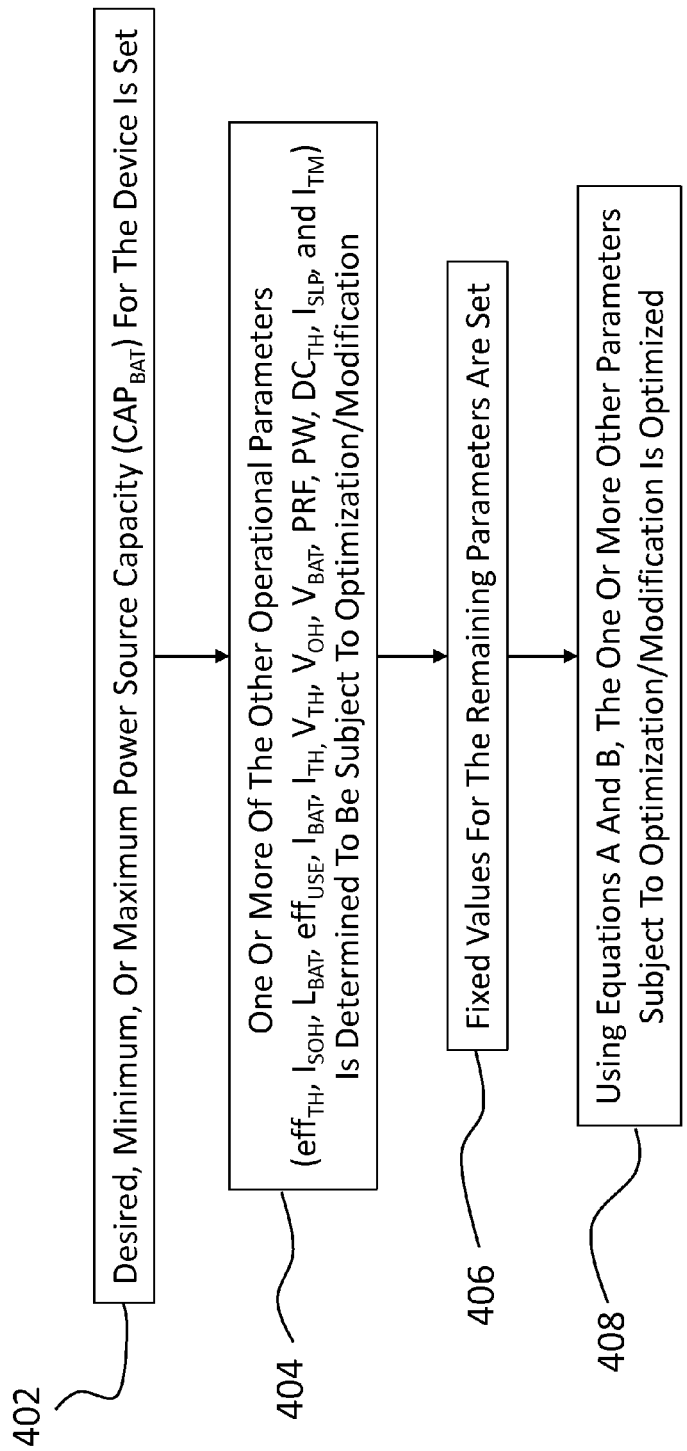
FIG. 4 is a flow chart illustrating the steps involved in one embodiment of setting a desired, minimum, or maximum power source capacity and optimizing one or more of the other operational parameters of an electro-medical device using the equations of the present specification.

In one embodiment, a desired, minimum, or maximum power source capacity for the device is set ($CAP_{BAT}$). Additionally, a minority, and preferably only one, of the remaining parameters ($eff_{TH}$, $I_{SOH}$, $L_{BAT}$, $eff_{USE}$, $I_{BAT}$, $I_{TH}$, $V_{TH}$, $V_{OH}$, $V_{BAT}$, PRF, PW, $DC_{TH}$, $I_{SLP}$, and $I_{TM}$) is subject to optimization or modification, with the remainder being a fixed value. Using the desired, minimum, or maximum power source capacity value and the other fixed values, the minority, or preferably one, of the parameters subject to optimization of modification is then determined using Equations A and B. FIG. 4 is a flow chart illustrating the steps involved in one embodiment of setting a desired, minimum, or maximum power source capacity and optimizing one or more of the other operational parameters of an electro-medical device using the equations of the present specification. At step 402, the desired, minimum, or maximum power source capacity ($CAP_{BAT}$) for the device is set. At step 404, one or more of the other parameters ($eff_{TH}$, $I_{SOH}$, $L_{BAT}$, $eff_{USE}$, $I_{BAT}$, $I_{TH}$, $V_{TH}$, $V_{OH}$, $V_{BAT}$, PRF, PW, $DC_{TH}$, $I_{SLP}$, and $I_{TM}$) is determined to be subject to optimization/modification. Then, at step 406, fixed values for the remaining parameters are set. Using equations A and B of the present specification, the one or more other parameters subject to optimization/modification is optimized at step 408.

Figure 5:
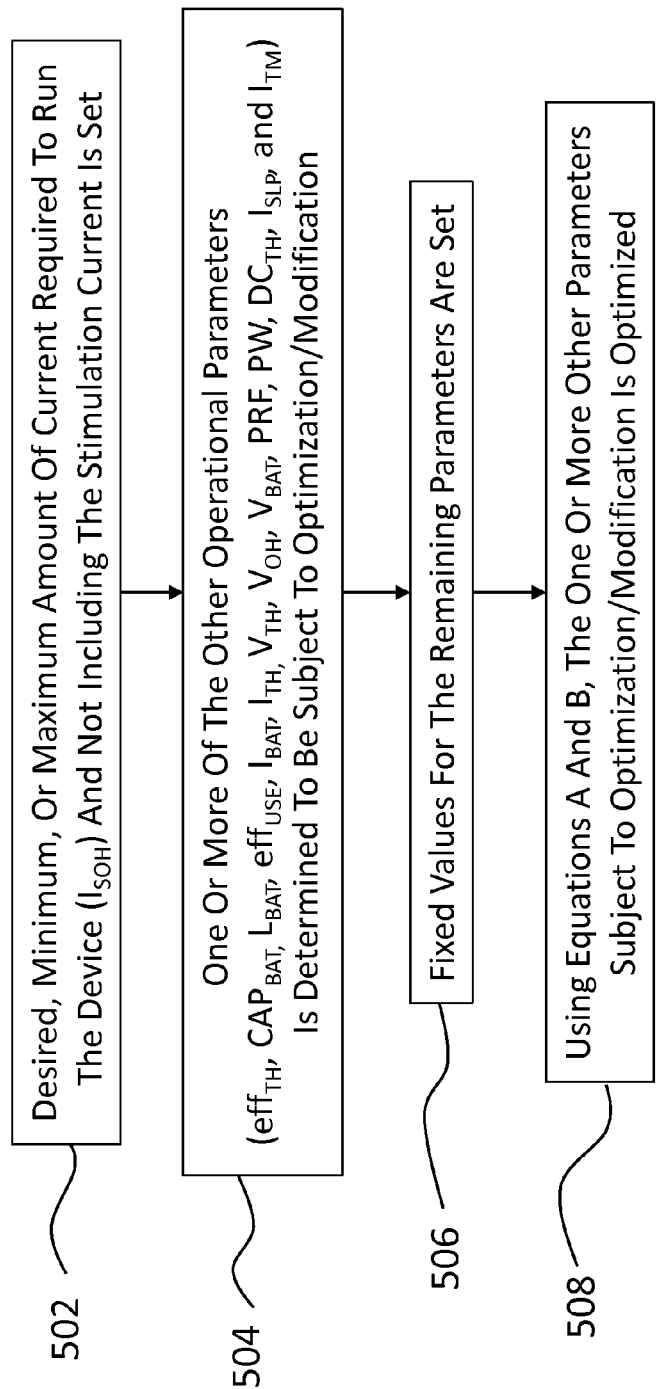
FIG. 5 is a flow chart illustrating the steps involved in one embodiment of setting a desired, minimum, or maximum amount of current required to run the device, and not including the stimulation current, and optimizing one or more of the other operational parameters of an electro-medical device using the equations of the present specification.

In one embodiment, a desired, minimum, or maximum amount of current required to run the device and not including the stimulation current is set ($I_{SOH}$). Additionally, a minority, and preferably only one, of the remaining parameters ($eff_{TH}$, $CAP_{BAT}$, $L_{BAT}$, $eff_{USE}$, $I_{BAT}$, $I_{TH}$, $V_{TH}$, $V_{OH}$, $V_{BAT}$, PRF, PW, $DC_{TH}$, $I_{SLP}$, and $I_{TM}$) is subject to optimization or modification, with the remainder being a fixed value. Using the desired, minimum, or maximum amount of current required to run the device, and not including the stimulation current, value and the other fixed values, the minority, or preferably one, of the parameters subject to optimization of modification is then determined using Equations A and B. FIG. 5 is a flow chart illustrating the steps involved in one embodiment of setting a desired, minimum, or maximum amount of current required to run the device, and not including the stimulation current, and optimizing one or more of the other operational parameters of an electro-medical device using the equations of the present specification. At step 502, the desired, minimum, or maximum amount of current required to run the device ($I_{SOH}$), and not including the stimulation current, is set. At step 504, one or more of the other parameters ($eff_{TH}$, $CAP_{BAT}$, $L_{BAT}$, $eff_{USE}$, $I_{BAT}$, $I_{TH}$, $V_{TH}$, $V_{OH}$, $V_{BAT}$, PRF, PW, $DC_{TH}$, $I_{SLP}$, and $I_{TM}$) is determined to be subject to optimization/modification. Then, at step 506, fixed values for the remaining parameters are set. Using equations A and B of the present specification, the one or more other parameters subject to optimization/modification is optimized at step 508.

Figure 6:
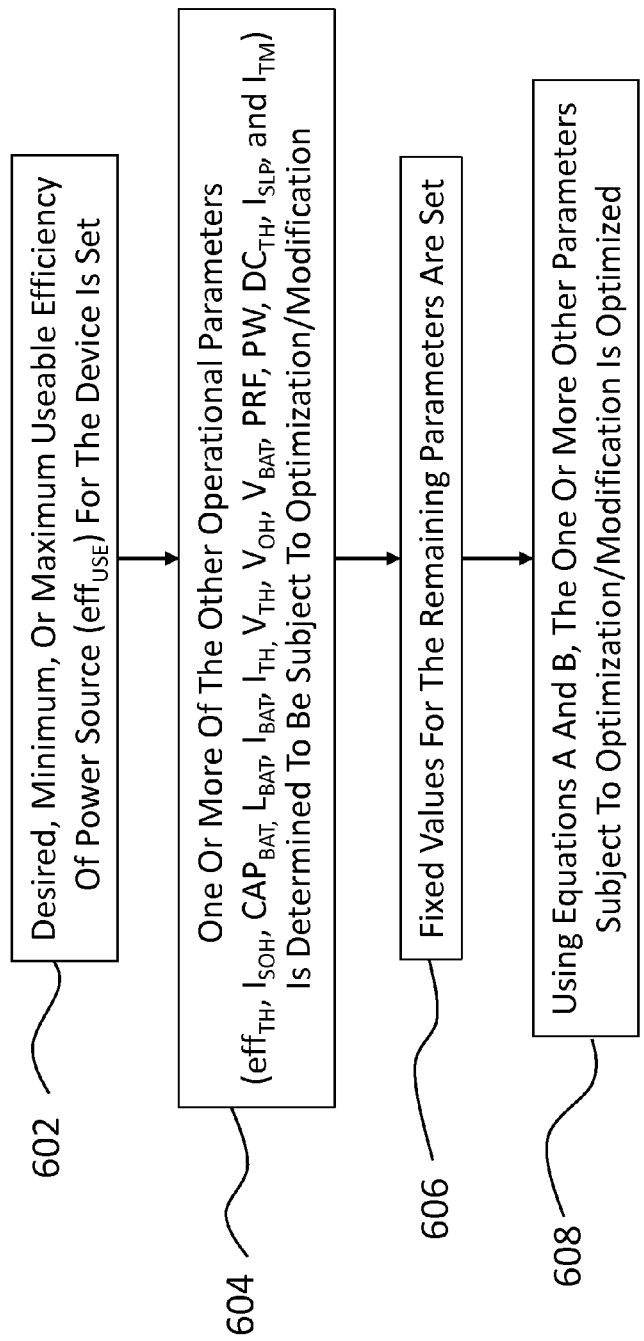
FIG. 6 is a flow chart illustrating the steps involved in one embodiment of setting a desired, minimum, or maximum useable efficiency of power source and optimizing one or more of the other operational parameters of an electro-medical device using the equations of the present specification.

In one embodiment, a desired, minimum, or maximum useable efficiency of power source is set ($eff_{USE}$). Additionally, a minority, and preferably only one, of the remaining parameters ($eff_{TH}$, $I_{SOH}$, $CAP_{BAT}$, $L_{BAT}$, $I_{BAT}$, $I_{TH}$, $V_{TH}$, $V_{OH}$, $V_{BAT}$, PRF, PW, $DC_{TH}$, $I_{SLP}$, and $I_{TM}$) is subject to optimization or modification, with the remainder being a fixed value. Using the desired, minimum, or maximum useable efficiency of power source value and the other fixed values, the minority, or preferably one, of the parameters subject to optimization of modification is then determined using Equations A and B. FIG. 6 is a flow chart illustrating the steps involved in one embodiment of setting a desired, minimum, or maximum useable efficiency of power source and optimizing one or more of the other operational parameters of an electro-medical device using the equations of the present specification. At step 602, the desired, minimum, or maximum useable efficiency of power source ($eff_{USE}$) for the device is set. At step 604, one or more of the other parameters ($eff_{TH}$, $CAP_{BAT}$, $L_{BAT}$, $I_{BAT}$, $I_{TH}$, $V_{TH}$, $V_{OH}$, $V_{BAT}$, PRF, PW, $DC_{TH}$, $I_{SLP}$, and $I_{TM}$) is determined to be subject to optimization/modification. Then, at step 606, fixed values for the remaining parameters are set. Using equations A and B of the present specification, the one or more other parameters subject to optimization/modification is optimized at step 608.

Figure 7:
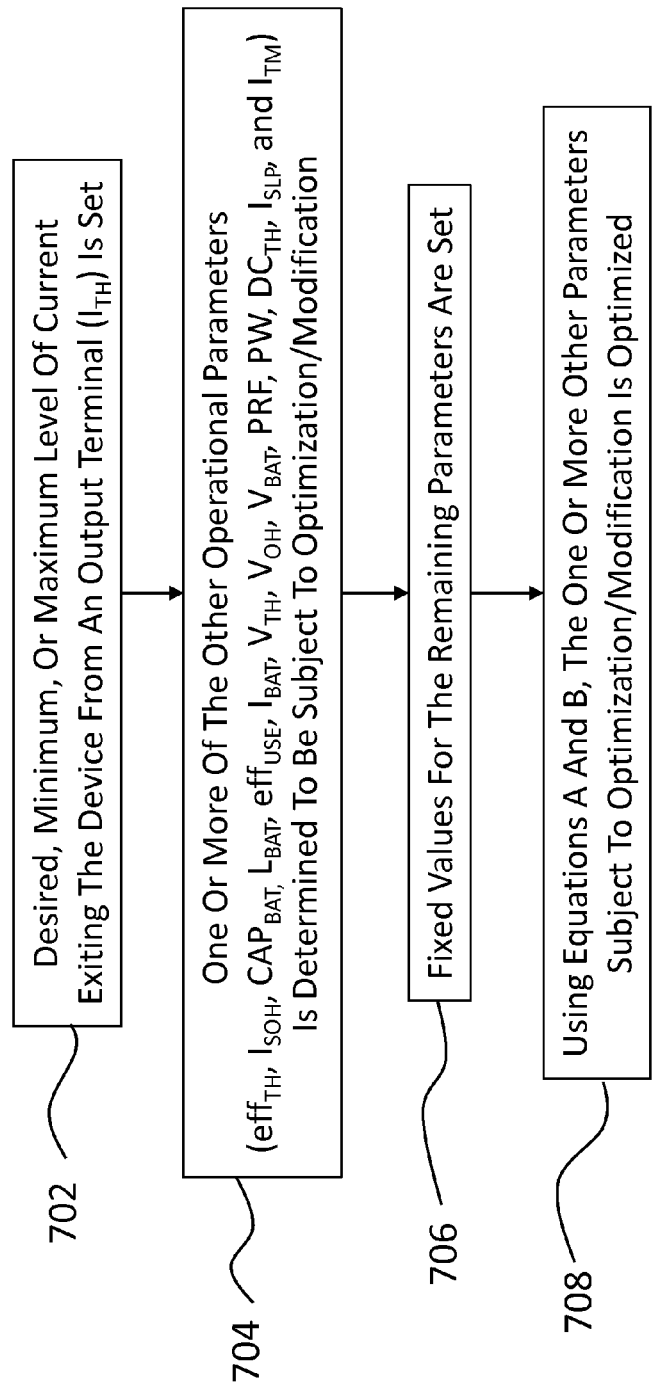
FIG. 7 is a flow chart illustrating the steps involved in one embodiment of setting a desired, minimum, or maximum level of current existing the device from an output terminal and optimizing one or more of the other operational parameters of an electro-medical device using the equations of the present specification.

In one embodiment, a desired, minimum, or maximum level of current exiting the device from an output terminal is set ($I_{TH}$). Additionally, a minority, and preferably only one, of the remaining parameters ($eff_{TH}$, $I_{SOH}$, $CAP_{BAT}$, $L_{BAT}$, $eff_{USE}$, $I_{BAT}$, $V_{TH}$, $V_{OH}$, $V_{BAT}$, PRF, PW, $DC_{TH}$, $I_{SLP}$, and $I_{TM}$) is subject to optimization or modification, with the remainder being a fixed value. Using the desired, minimum, or maximum level of current exiting the device from an output terminal value and the other fixed values, the minority, or preferably one, of the parameters subject to optimization of modification is then determined using Equations A and B. FIG. 7 is a flow chart illustrating the steps involved in one embodiment of setting a desired, minimum, or maximum level of current existing the device from an output terminal and optimizing one or more of the other operational parameters of an electro-medical device using the equations of the present specification. At step 702, the desired, minimum, or maximum level of current exiting the device from an output terminal ($I_{TH}$) is set. At step 704, one or more of the other parameters ($eff_{TH}$, $CAP_{BAT}$, $L_{BAT}$, $eff_{USE}$, $I_{BAT}$, $V_{TH}$, $V_{OH}$, $V_{BAT}$, PRF, PW, $DC_{TH}$, $I_{SLP}$, and $I_{TM}$) is determined to be subject to optimization/modification. Then, at step 706, fixed values for the remaining parameters are set. Using equations A and B of the present specification, the one or more other parameters subject to optimization/modification is optimized at step 708.

Figure 8:
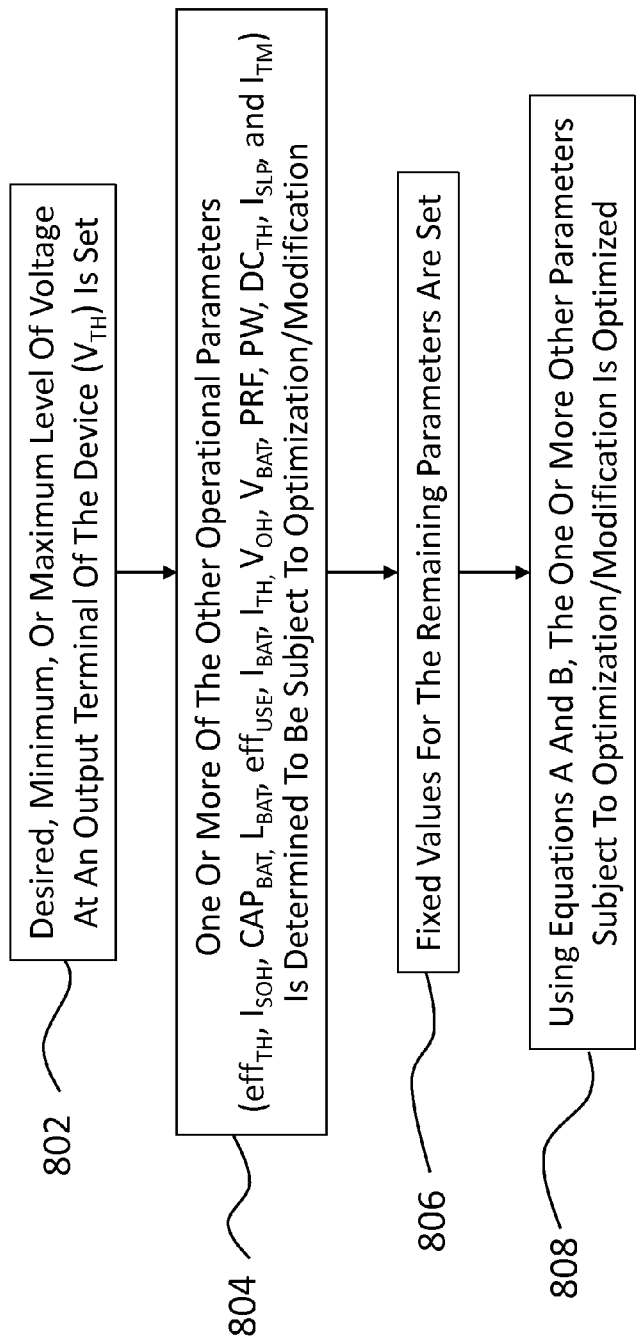
FIG. 8 is a flow chart illustrating the steps involved in one embodiment of setting a desired, minimum, or maximum level of voltage at an output terminal of the device and optimizing one or more of the other operational parameters of an electro-medical device using the equations of the present specification.

In one embodiment, a desired, minimum, or maximum level of voltage at an output terminal of the device is set ($V_{TH}$). Additionally, a minority, and preferably one, of the remaining parameters ($eff_{TH}$, $I_{SOH}$, $CAP_{BAT}$, $L_{BAT}$, $eff_{USE}$, $I_{BAT}$, $I_{TH}$, $V_{OH}$, $V_{BAT}$, PRF, PW, $DC_{TH}$, $I_{SLP}$, and $I_{TM}$) is subject to optimization or modification, with the remainder being a fixed value. Using the desired, minimum, or maximum level of voltage at an output terminal of the device value and the other fixed values, the minority, or preferably one, of the parameters subject to optimization of modification is then determined using Equations A and B. FIG. 8 is a flow chart illustrating the steps involved in one embodiment of setting a desired, minimum, or maximum level of voltage at an output terminal of the device and optimizing one or more of the other operational parameters of an electro-medical device using the equations of the present specification. At step 802, the desired, minimum, or maximum level of voltage at an output terminal of the device ($V_{TH}$) is set. At step 804, one or more of the other parameters (eff$_{TM}$, $I_{SOH}$, CAP$_{BAT}$, $L_{BAT}$, eff$_{USE}$, $I_{BAT}$, $I_{TH}$, $V_{OH}$, $V_{BAT}$, PRF, PW, DC$_{TH}$, $I_{SLP}$, and $I_{TM}$) is determined to be subject to optimization/modification. Then, at step 806, fixed values for the remaining parameters are set. Using equations A and B of the present specification, the one or more other parameters subject to optimization/modification is optimized at step 808.

Figure 9:
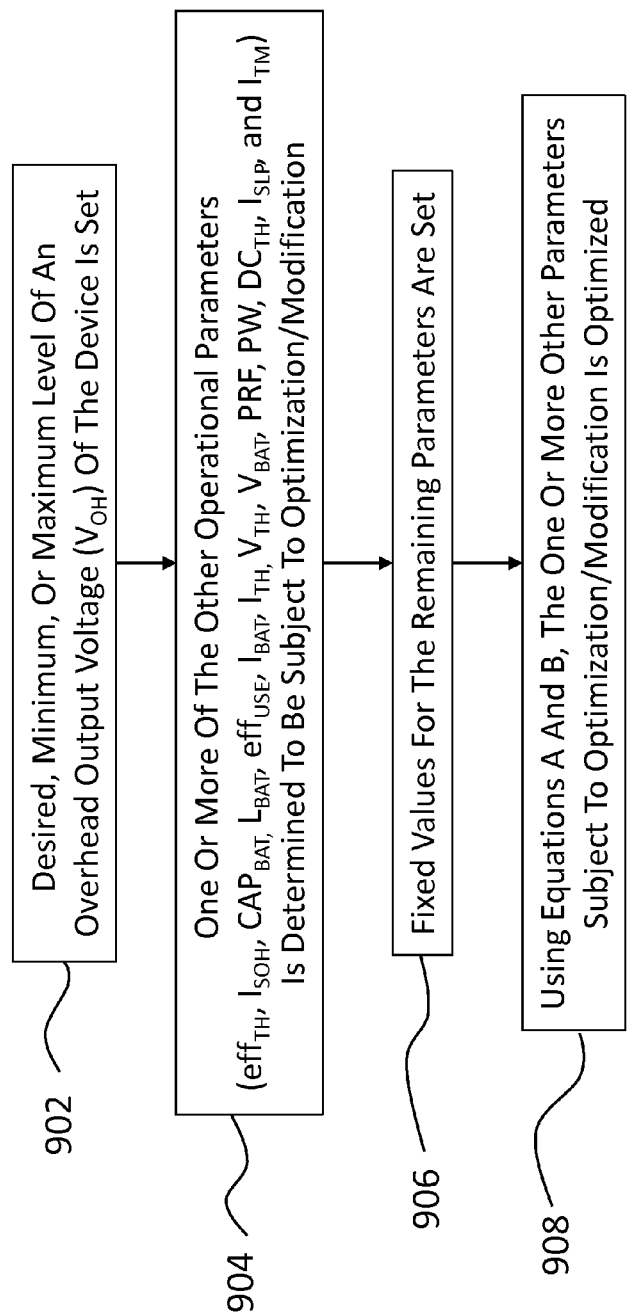
FIG. 9 is a flow chart illustrating the steps involved in one embodiment of setting a desired, minimum, or maximum level of an overhead output voltage and optimizing one or more of the other operational parameters of an electro-medical device using the equations of the present specification.

In one embodiment, a desired, minimum, or maximum level of an overhead output voltage is set ($V_{OH}$). Additionally, a minority, and preferably only one, of the remaining parameters (eff$_{TM}$, $I_{SOH}$, CAP$_{BAT}$, $L_{BAT}$, eff$_{USE}$, $I_{BAT}$, $I_{TH}$, $V_{TH}$, $V_{BAT}$, PRF, PW, DC$_{TH}$, $I_{SLP}$, and $I_{TM}$) is subject to optimization or modification, with the remainder being a fixed value. Using the desired, minimum, or maximum level of an overhead output voltage value and the other fixed values, the minority, or preferably one, of the parameters subject to optimization of modification is then determined using Equations A and B. FIG. 9 is a flow chart illustrating the steps involved in one embodiment of setting a desired, minimum, or maximum level of an overhead output voltage and optimizing one or more of the other operational parameters of an electro-medical device using the equations of the present specification. At step 902, the desired, minimum, or maximum level of an overhead output voltage ($V_{OH}$) of the device is set. At step 904, one or more of the other parameters (eff$_{TM}$, $I_{SOH}$, CAP$_{BAT}$, $L_{BAT}$, eff$_{USE}$, $I_{BAT}$, $I_{TH}$, $V_{TH}$, $V_{BAT}$, PRF, PW, DC$_{TH}$, $I_{SLP}$, and $I_{TM}$) is determined to be subject to optimization/modification. Then, at step 906, fixed values for the remaining parameters are set. Using equations A and B of the present specification, the one or more other parameters subject to optimization/modification is optimized at step 908.

Figure 10:
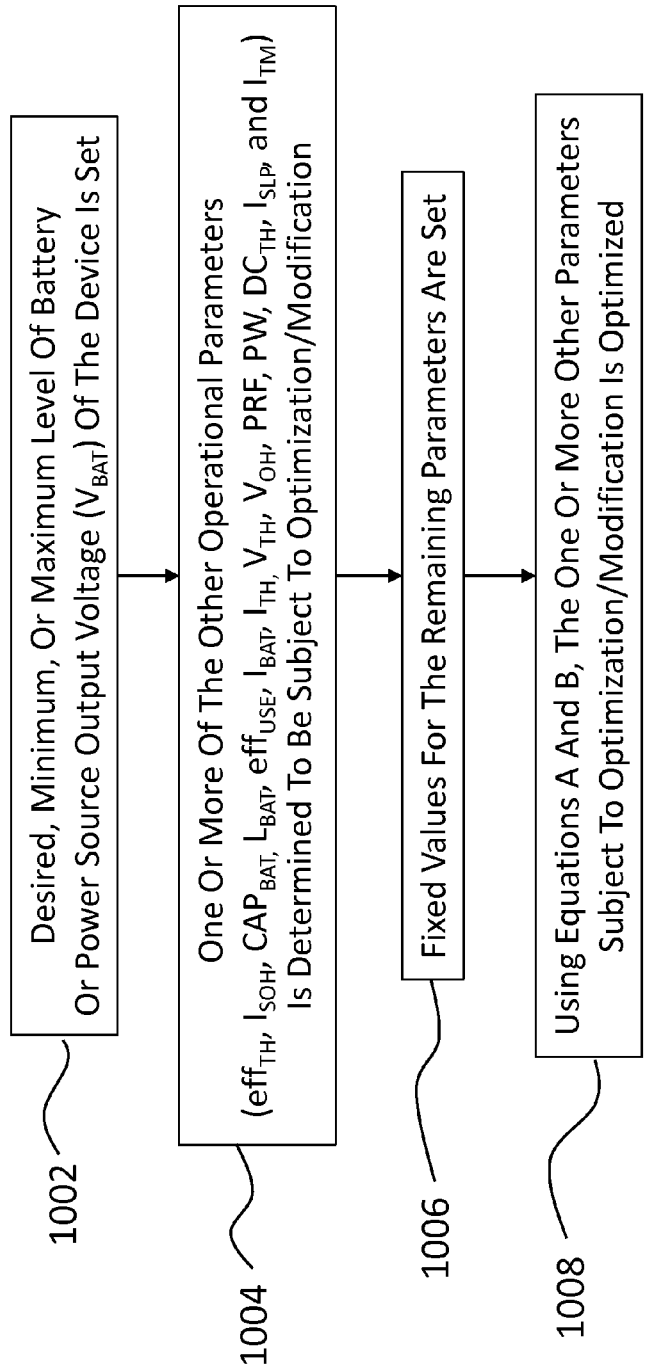
FIG. 10 is a flow chart illustrating the steps involved in one embodiment of setting a desired, minimum, or maximum level of battery or power source output voltage and optimizing one or more of the other operational parameters of an electro-medical device using the equations of the present specification.

In one embodiment, a desired, minimum, or maximum level of battery or power source voltage is set ($V_{BAT}$). Additionally, a minority, and preferably only one, of the remaining parameters (eff$_{TM}$, $I_{SOH}$, CAP$_{BAT}$, $L_{BAT}$, eff$_{USE}$, $I_{BAT}$, $I_{TH}$, $V_{TH}$, $V_{OH}$, PRF, PW, DC$_{TH}$, $I_{SLP}$, and $I_{TM}$) is subject to optimization or modification, with the remainder being a fixed value. Using the desired, minimum, or maximum level of battery or power source voltage value and the other fixed values, the minority, or preferably one, of the parameters subject to optimization of modification is then determined using Equations A and B. FIG. 10 is a flow chart illustrating the steps involved in one embodiment of setting a desired, minimum, or maximum level of battery or power source output voltage and optimizing one or more of the other operational parameters of an electro-medical device using the equations of the present specification. At step 1002, the desired, minimum, or maximum level of battery or power source output voltage ($V_{BAT}$) of the device is set. At step 1004, one or more of the other parameters (eff$_{TH}$, $I_{SOH}$, CAP$_{BAT}$, $L_{BAT}$, eff$_{USE}$, $I_{BAT}$, $I_{TH}$, $V_{TH}$, $V_{OH}$, PRF, PW, DC$_{TH}$, $I_{SLP}$, and $I_{TM}$) is determined to be subject to optimization/modification. Then, at step 1006, fixed values for the remaining parameters are set. Using equations A and B of the present specification, the one or more other parameters subject to optimization/modification is optimized at step 1008.

Figure 11:
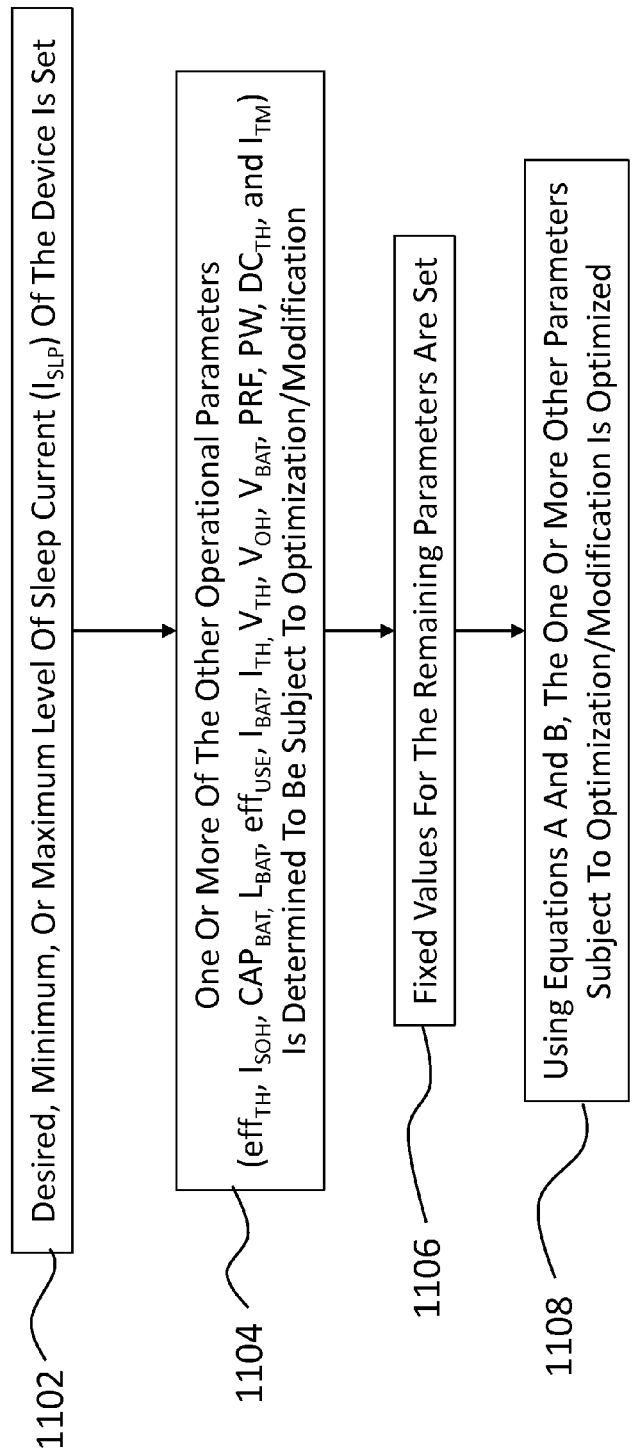
FIG. 11 is a flow chart illustrating the steps involved in one embodiment of setting a desired, minimum, or maximum level of sleep current and optimizing one or more of the other operational parameters of an electro-medical device using the equations of the present specification.

In one embodiment, a desired, minimum, or maximum level of sleep current is set ($I_{SLP}$). Additionally, a minority, and preferably only one, of the remaining parameters (eff$_{TH}$, $I_{SOH}$, CAP$_{BAT}$, $L_{BAT}$, eff$_{USE}$, $I_{BAT}$, $I_{TH}$, $V_{TH}$, $V_{OH}$, $V_{BAT}$, PRF, PW, DC$_{TH}$, and $I_{TM}$) is subject to optimization or modification, with the remainder being a fixed value. Using the desired, minimum, or maximum level of sleep current value and the other fixed values, the minority, or preferably one, of the parameters subject to optimization of modification is then determined using Equations A and B. FIG. 11 is a flow chart illustrating the steps involved in one embodiment of setting a desired, minimum, or maximum level of sleep current and optimizing one or more of the other operational parameters of an electro-medical device using the equations of the present specification. At step 1102, the desired, minimum, or maximum level of sleep current ($I_{SLP}$) of the device is set. At step 1104, one or more of the other parameters (eff$_{TH}$, $I_{SOH}$, CAP$_{BAT}$, $L_{BAT}$, eff$_{USE}$, $I_{BAT}$, $I_{TH}$, $V_{TH}$, $V_{OH}$, $V_{BAT}$, PRF, PW, DC$_{TH}$, and $I_{TM}$) is determined to be subject to optimization/modification. Then, at step 1106, fixed values for the remaining parameters are set. Using equations A and B of the present specification, the one or more other parameters subject to optimization/modification is optimized at step 1108.

Figure 12:
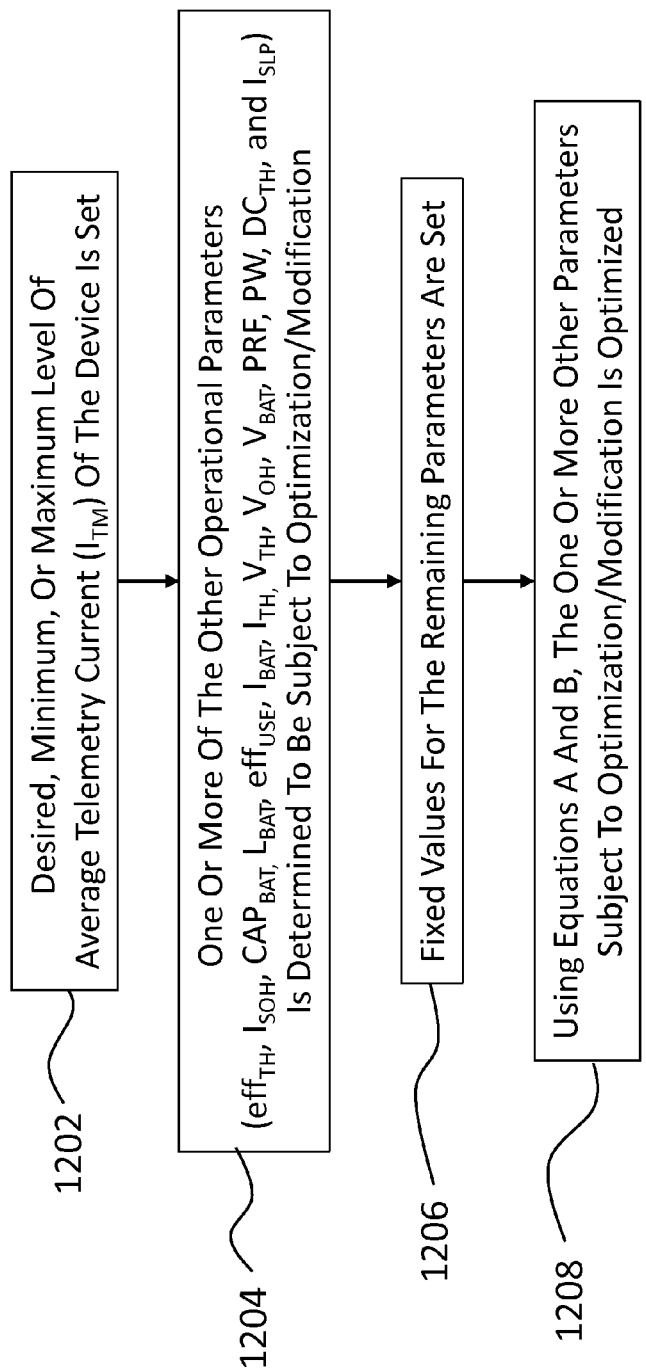
FIG. 12 is a flow chart illustrating the steps involved in one embodiment of setting a desired, minimum, or maximum level of average telemetry current and optimizing one or more of the other operational parameters of an electro-medical device using the equations of the present specification.

In one embodiment, a desired, minimum, or maximum level of average telemetry current is set ($I_{TM}$). Additionally, a minority, and preferably only one, of the remaining parameters (eff$_{TH}$, $I_{SOH}$, CAP$_{BAT}$, $L_{BAT}$, eff$_{USE}$, $I_{BAT}$, $I_{TH}$, $V_{TH}$, $V_{OH}$, $V_{BAT}$, PRF, PW, DC$_{TH}$, and $I_{SLP}$) is subject to optimization or modification, with the remainder being a fixed value. Using the desired, minimum, or maximum level of average telemetry current value and the other fixed values, the minority, or preferably one, of the parameters subject to optimization of modification is then determined using Equations A and B. FIG. 12 is a flow chart illustrating the steps involved in one embodiment of setting a desired, minimum, or maximum level of average telemetry current and optimizing one or more of the other operational parameters of an electro-medical device using the equations of the present specification. At step 1202, the desired, minimum, or maximum level of average telemetry current ($I_{TM}$) of the device is set. At step 1204, one or more of the other parameters (eff$_{TH}$, $I_{SOH}$, CAP$_{BAT}$, $L_{BAT}$, eff$_{USE}$, $I_{BAT}$, $I_{TH}$, $V_{TH}$, $V_{OH}$, $V_{BAT}$, PRF, PW, DC$_{TH}$, and $I_{SLP}$) is determined to be subject to optimization/modification. Then, at step 1206, fixed values for the remaining parameters are set. Using equations A and B of the present specification, the one or more other parameters subject to optimization/modification is optimized at step 1208.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A device for electrical stimulation of one or more anatomical target sites in a patient and for use in treating a plurality of biological conditions of the patient, said device comprising:
   a pulse generator providing electrical stimulation to said one or more anatomical target sites, wherein said electrical stimulation comprises a stimulation current;
   a power source for powering said pulse generator;
   at least one stimulator electrode connected to said pulse generator, wherein said at least one stimulator electrode is configured to apply said electrical stimulation to said one or more anatomical target sites; and, a microprocessor programmed to vary a plurality of therapy protocol parameters governing the electrical stimulation to thereby modify operational life parameters of the power source, wherein the therapy protocol parameters and the operational life of the power source are associated according to the following relations:

$$L_{BAT} = \frac{CAP_{BAT} \cdot \mathit{eff}_{USE}}{I_{BAT}}, \text{ where}$$

$$I_{BAT} = \left[\left[\left(\mathit{eff}_{TH} \cdot I_{TH} \cdot \frac{V_{TH} + V_{OH}}{V_{BAT}} \cdot PRF \cdot PW\right) + I_{SOH}\right] \cdot DC_{TH} + I_{SLP} \cdot (1 - DC_{TH}) + I_{TM}\right]$$

wherein $\mathit{eff}_{TH}$ is a function of an output stimulation circuit current divided by an input stimulation circuit current; wherein $I_{SOH}$ is equal to an amount of current required to run the device and not including the stimulation current; wherein $L_{BAT}$ is a function of power source service life; wherein $CAP_{BAT}$ is a function of power source capacity; wherein $\mathit{eff}_{USE}$ is a function of a usable efficiency of power source; wherein $I_{BAT}$ is a function of power source current; wherein $I_{TH}$ is a function of a level of current exiting the device from an output terminal; wherein $V_{TH}$ is a function of a level of voltage at an output terminal of the device; wherein $V_{OH}$ is a function of an overhead output voltage; wherein $V_{BAT}$ is a function of a power source voltage; wherein PRF is a function of a pulse repetition frequency; wherein PW is a function of a pulse width; wherein $DC_{TH}$ is a function of a duty cycle; wherein $I_{SLP}$ is a function of sleep current; and wherein $I_{TM}$ is a function of average telemetry current.

2. The device of claim 1, wherein said power source is a battery.

3. The device of claim 2, wherein said battery is rechargeable.

4. The device of claim 2, wherein said battery is non-rechargeable.

5. The device of claim 2, wherein the operational life parameters of the battery comprise battery capacity, usable efficiency of battery due to end of life efficiency, and battery current.

6. The device of claim 1, wherein said power source is a capacitor.

7. The device of claim 1, wherein said therapy protocol parameters for an electrical stimulation pulse train comprise: number of pulses, shape of pulses, interval between pulse train repetitions, duration of a pulse, timing and amplitude of pulses, amperage to be provided to said one or more anatomical target sites, potential to be provided to said one or more anatomical target sites, and duty cycles.

8. The device of claim 1, further comprising at least one sensor in data communication with said microprocessor, wherein the at least one sensor is configured to monitor at least one physiological parameter of said patient.

9. The device of claim 8, wherein said microprocessor modifies said therapy protocol parameters based upon physiological information sensed by said at least one sensor.

10. A device for electrical stimulation of one or more anatomical target sites in a patient and for use in treating a plurality of biological conditions of the patient, said device comprising:

a pulse generator providing electrical stimulation to said one or more anatomical target sites;

a power source for powering said pulse generator;

at least one stimulator electrode connected to said pulse generator, wherein said at least one stimulator electrode is configured to apply the electrical stimulation to said one or more anatomical target sites;

a microprocessor programmed to vary a plurality of therapy protocol parameters governing the electrical stimulation to thereby modify operational life parameters of the power source, wherein the therapy protocol parameters and the operational life of the power source are associated according to the following relations:

$$L_{BAT} = \frac{CAP_{BAT} \cdot \mathit{eff}_{USE}}{I_{BAT}}, \text{ where}$$

$$I_{BAT} = \left[\left[\left(\mathit{eff}_{TH} \cdot I_{TH} \cdot \frac{V_{TH} + V_{OH}}{V_{BAT}} \cdot PRF \cdot PW\right) + I_{SOH}\right] \cdot DC_{TH} + I_{SLP} \cdot (1 - DC_{TH}) + I_{TM}\right];$$

and, at least one sensor connected to said microprocessor, wherein the at least one sensor is configured to sense at least one physiological parameter of said patient;

wherein $\mathit{eff}_{TH}$ is a function of an output stimulation circuit current divided by an input stimulation circuit current; wherein $I_{SOH}$ is equal to an amount of current required to run the device and not including the stimulation current; wherein $L_{BAT}$ is a function of power source service life; wherein $CAP_{BAT}$ is a function of power source capacity; wherein $\mathit{eff}_{USE}$ is a function of a usable efficiency of power source; wherein $I_{BAT}$ is a function of power source current; wherein $I_{TH}$ is a function of a level of current exiting the device from an output terminal; wherein $V_{TH}$ is a function of a level of voltage at an output terminal of the device; wherein $V_{OH}$ is a function of an overhead output voltage; wherein $V_{BAT}$ is a function of a power source voltage; wherein PRF is a function of a pulse repetition frequency; wherein PW is a function of a pulse width; wherein $DC_{TH}$ is a function of a duty cycle; wherein $I_{SLP}$ is a function of sleep current; and wherein $I_{TM}$ is a function of average telemetry current.

11. The device of claim 10, wherein said power source is a battery.

12. The device of claim 11, wherein said battery is rechargeable.

13. The device of claim 11, wherein said battery is non-rechargeable.

14. The device of claim 11, wherein the operational life parameters of the battery comprise battery capacity, usable efficiency of battery due to end of life efficiency, and battery current.

15. The device of claim 10, wherein said power source is a capacitor.

16. The device of claim 10, wherein said therapy protocol parameters for an electrical stimulation pulse train comprise: number of pulses, shape of pulses, interval between pulse train repetitions, duration of a pulse, timing and amplitude of pulses, amperage to be provided to said one or more anatomical target sites, potential to be provided to said one or more anatomical target sites, and duty cycles.

17. A system for electrical stimulation of one or more anatomical target sites in a patient and for use in treating a plurality of biological conditions of the patient, said system comprising:
- a pulse generator providing electrical stimulation to said one or more anatomical target sites;
- a power source for powering said pulse generator;
- at least one stimulator electrode connected to said pulse generator, wherein the at least one stimulator electrode is configured to apply said electrical stimulation to said one or more anatomical target sites; and,
- a microprocessor programmed to vary a plurality of therapy protocol parameters governing the electrical stimulation to thereby modify operational life parameters of the power source, wherein the therapy protocol parameters and the operational life of the power source are associated according to the following relations:

$$L_{BAT} = \frac{CAP_{BAT} \cdot \mathit{eff}_{USE}}{I_{BAT}}, \text{ where}$$

$$I_{BAT} = \left[\left[\left(\mathit{eff}_{TH} \cdot I_{TH} \cdot \frac{V_{TH} + V_{OH}}{V_{BAT}} \cdot PRF \cdot PW\right) + I_{SOH}\right] \cdot DC_{TH} + I_{SLP} \cdot (1 - DC_{TH}) + I_{TM}\right]$$

wherein $\mathit{eff}_{TH}$ is a function of an output stimulation circuit current divided by an input stimulation circuit current; wherein $I_{SOH}$ is equal to an amount of current required to run the device and not including the stimulation current; wherein $L_{BAT}$ is a function of power source service life; wherein $CAP_{BAT}$ is a function of power source capacity; wherein $\mathit{eff}_{USE}$ is a function of a usable efficiency of power source; wherein $I_{BAT}$ is a function of power source current; wherein $I_{TH}$ is a function of a level of current exiting the device from an output terminal; wherein $V_{TH}$ is a function of a level of voltage at an output terminal of the device; wherein $V_{OH}$ is a function of an overhead output voltage; wherein $V_{BAT}$ is a function of a power source voltage; wherein PRF is a function of a pulse repetition frequency; wherein PW is a function of a pulse width; wherein $DC_{TH}$ is a function of a duty cycle; wherein $I_{SLP}$ is a function of sleep current; and wherein $I_{TM}$ is a function of average telemetry current.

18. The system of claim 17, wherein said power source is a battery.

19. The system of claim 18, wherein said battery is rechargeable.

20. The system of claim 18, wherein said battery is non-rechargeable.

21. The device of claim 17, wherein said power source is a capacitor.

22. The system of claim 17, further comprising at least one sensor in data communication with the microprocessor, wherein the at least one sensor is configured to monitor at least one physiological parameter of said patient.

23. The system of claim 22, wherein said microprocessor modifies said therapy protocol parameters based upon physiological information sensed by said at least one sensor.

* * * * *